(12) United States Patent
Nelson et al.

(10) Patent No.: US 7,985,768 B2
(45) Date of Patent: Jul. 26, 2011

(54) COMPOUNDS AS CANNABINOID RECEPTOR LIGANDS

(75) Inventors: Derek W. Nelson, Highland Park, IL (US); Steven P. Latshaw, Round Lake Beach, IL (US)

(73) Assignee: Abbott Laboratories, Abbott Park, IL (US)

( * ) Notice: Subject to any disclaimer, the term of this patent is extended or adjusted under 35 U.S.C. 154(b) by 970 days.

(21) Appl. No.: 11/848,512

(22) Filed: Aug. 31, 2007

(65) Prior Publication Data
US 2008/0058308 A1   Mar. 6, 2008

Related U.S. Application Data

(60) Provisional application No. 60/841,666, filed on Aug. 31, 2006.

(51) Int. Cl.
A61K 31/381 (2006.01)
C07D 495/04 (2006.01)

(52) U.S. Cl. .......................................... 514/443; 549/50
(58) Field of Classification Search .................. 514/443; 549/50
See application file for complete search history.

(56) References Cited

U.S. PATENT DOCUMENTS

| 6,559,186 B1 | 5/2003 | Campbell |
| 2008/0312435 A1 | 12/2008 | Saito et al. |

FOREIGN PATENT DOCUMENTS

| EP | 412404 A2 | 2/1991 |
| EP | 568096 A1 | 11/1993 |
| EP | 1219612 A1 | 7/2002 |
| FR | 2796643 A1 | 1/2001 |
| WO | WO-2005023818 A2 | 3/2005 |
| WO | WO-2005058887 A1 | 6/2005 |
| WO | WO-2006051704 A1 | 5/2006 |
| WO | WO-2006070106 A1 | 7/2006 |

OTHER PUBLICATIONS

"IUPAC Commission on Nomenclature of Organic Chemistry Rules for the Nomenclature of Organic Chemistry, Section E: Stereochemistry (Recommendations 1974)," Pure Appl Chem, 1976, 13-30, vol. 45.
Ambartsumova, R.F. et al., "Effect of Various Factors on the Reaction of 2-Aminobenzothiazoles with Propylene Oxide," Chemistry of Heterocyclic Compounds, 2002, 994-999, vol. 38—Issue 8.
Ansell M.F. and Mason J.S., "The Synthesis of (+/−)-10a-Homo-11a-carbathromboxane A1, a Stable Thromboxane A Analogue," J Chem Soc Perkin Trans I, 1984, 1061-1068.
Arevalo-Martin, A., et al., "Therapeutic Action of Cannabinoids in a Murine Model of Multiple Sclerosis," Journal of Neuroscience, 2003, 2511-2516, vol. 23, No. 7.
Baker, T.J. et al., "Regiospecific Vinyl Phosphate/β-Keto Phosphonate Rearrangements Initiated by Halogen-Metal Exchange," Journal of Organic Chemistry, 1998, 2613-2618, vol. 63—Issue 8.

Benito, C, et al., "A Glial Endogenous Cannabinoid System Is Upregulated in the Brains of Macaques with Simian Immunodeficiency Virus-Induced Encephalitis," Journal of Neuroscience, 2005, 2530-2536, vol. 25—Issue 10.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.
Bouchard, J-F et al., "Contribution of endocannabinoids in the endothelial protection afforded by ischemic preconditioning in the isolated rat heart", Life Sciences, 2003, 1859-1870, vol. 72.
Boyle, W.J. et al., "Osteoclast differentiation and activation," (Binary/Image), 2003, 337-342, vol. 423.
Brennan, T.J. et al., "Characterization of a rat model of incisional pain," (Binary/Image), 1996, 493-501, vol. 64.
Buckley, N. E. et al., "Immunomodulation by cannabinoids is absent in mice deficient for the cannabinoid CB receptor," European Journal of Pharmacology, 2000, 141-149, vol. 396.
Carlisle, S.J. et al., "Differential expression of the CB2 cannabinoid receptor by rodent macrophages and macrophage-like cells in relation to cell activation," International Immunopharmacology, 2002, 69, vol. 2.
Carrier, E.J. et al., "Endocannabinoids in Neuroimmunology and Stress," Current Drug Targets CNS and Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Cichewicz, D.L. et al., "Synergistic interactions between cannabinoid and opioid analgesics," Life Sciences, 2004, 1317-1324, vol. 74.
Clayton, N. et al., "CB1 and CB2 cannabinoid receptors are implicated in inflammatory pain," (Binary/Image), 2002, 253-260, vol. 96.

(Continued)

*Primary Examiner* — Taofiq A Solola
(74) *Attorney, Agent, or Firm* — Nancy J. Gettel; Andrew M. Parial; Soanli Srivastava

(57) ABSTRACT

The present invention relates to thiophene containing compounds of formula (I)

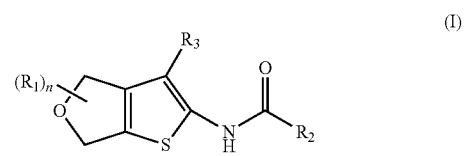

wherein $R_1$, $R_2$, $R_3$, and n are as defined in the specification, pharmaceutical compositions comprising such compounds, and methods of treating conditions and disorders using such compounds and pharmaceutical compositions.

21 Claims, No Drawings

OTHER PUBLICATIONS

Dixon, W.J. "Efficient analysis of experimental observations," Annual Review of Pharmacology and Toxicology, 1980, 441-462, vol. 20.

Dorsch, J.B., McElvain, S.M., "The Preparation of Benzoylacetic Ester and Some of its Homologs," J Am Chem Soc, 1932, 2960-2964, 54.

Fattori D., Henry S., Vogel P., "The Demjanov and Tiffeneau-Demjanov one-carbon ring enlargements of 2-aminomethyl-7-oxabicyclo[2.2.1]heptane derivatives. The stereo- and regioselective additions of 8-oxabicyclo[3.2.1]oct-6-en-2-one to soft electrophiles. ," Tetrahedron, 1993, 1649-1664, 49/8, Pergamon Press Ltd.

Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.

Galiégue, et al., "Expression of central and peripheral cannabinoid receptors in human immune tissues and leukocyte subpopulations," European Journal of Biochemistry, 1995, 54-61, vol. 232.

Golech, S.A. et al., "Human brain endothelium: coexpression and function of vannilloid and endocannabinoid receptors," Molecular Brain Research, 2004, 87-92, vol. 132.

Greene, T.W. et al., "Protective Groups in Organic Synthesis", 1999, 3 rd Ed, 494-653.

Grotenhermen, F. et al., "IACM 2nd Conference on Cannabinoids in Medicine," Expert Opinion in Pharmacotherapy, 2003, 2367-2371, vol. 4—Issue 12.

Hanus, L. et al., "HU-308: A specific agonist for CB 2, a peripheral cannabinoid receptor," Proceedings of the National Academy of Science, 1999, 14228-14233, vol. 96.

Hargreaves, et al., "A new and sensitive method for measuring thermal nociception in cutaneous hyperalgesia," (Binary/Image), 1988, 77-88, vol. 32.

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.

Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.

Idris, A.I. et al., "Regulation of bone mass, bone loss and osteoclast activity by cannabinoid receptors," Nature Medicine, 2005, 774-779, vol. 11—Issue 7.

Ihenetu, K. et al., "Inhibition of interleukin-8 release in the human colonic epithelial cell line HT-29 by cannabinoids," European Journal of Pharmacology, 2003, 207-215, vol. 458.

International Search Report for application No. PCT/US2007/0077321, Mailed on Jan. 2, 2008, 3 pages.

International Search Report, European Patent Office (Nov. 27, 2008).

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14—Issue 22.

Kim, S.H. and Chung, J.M. "An experimental model for peripheral neuropathy produced by segmental spinal nerve ligation in the rat," (Binary/Image), 1992, 355-363, vol. 50—Issue 3.

Kreutzberg, G W "Microglia: a sensor for pathological events in the CNS," Trends in Neuroscience, 1996, 312-318, vol. 19.

Lepicier, P. et al., "Endocannabinoids protect the rat isolated heart against ischaemia," British Journal of Pharmacology, 2003, 805-815, vol. 139.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 627-634, vol. 15—Issue 2.

Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23—Issue 16.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Nunez, E. et al., "Cannabinoid CB2 Receptors Are Expressed by Perivascular Microglial Cells in the Human Brain: An Immunohistochemical Study," Synapse, 2004, 208-213, vol. 53.

Partch, Ret al., "2-Oxaadamantane-1-N,N,N-trimethylmethanaminium Iodide:1 Synthesis and Potential for Muscarinic Activity," Croatia Chemical Acta, 1985, 661-669, vol. 58—Issue 4.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology and Therapeutics, 2002, 165-174, vol. 95.

Prescott, et al., "Lipid Vesicles as Carriers for Introducing Biologically Active Materials into Cells," Methods in Cell Biology, 1976, 33-71, vol. 14, Academic Press.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Genetic determinants of susceptibility to osteoporosis," Current Opinion in Pharmacology, 2003, 286-290, vol. 3.

Ralston, S.H. "Regulation of bone mass, bone loss and osteoclast activity by cannabinoid receptors," Nature Medicine, 2005, 774-779, vol. 11.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.

Sabnis, R.W. et al., "2-Aminothiophenes by the Gewald Reaction," J Heterocyclic Chemistry, 1999, 333-345, 36, Wiley.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.

Walter L. et al., "Cannabinoids and neuroinflammation," Pharmacology, 2004, 775-785, vol. 141.

Warhurst A.C. et al., "Interferon ? induces differential upregulation of a and β chemokine secretion in colonic epithelial cell lines," (Binary/Image), 1998, 208-213, vol. 42.

Watkins L.R. et al., "Glial activation: a driving force for pathological pain," Trends in Neuroscience, 2001, 450-455, vol. 24—Issue 8.

Werbel L.M. et al., "1-Alkyl-3-(3-alkyl-5-nitro-4-thiazolin-2-ylidene)-ureas and Related compounds as Schistosomicides" Journal of Medicinal Chemistry, 1972, 955-963, vol. 15—Issue 9.

Weyer et al., "Blutzuckersenkende Chinolin-8-carboxamidoalkyl-benzol sulfonamid derivate", Arzneimittel-Forschung, 1974, vol. 24, 269-275.

Williams K. et al., "Central nervous system perivascular cells are immunoregulatory cells that connect the CNS with the peripheral immune system," (Binary/Image), 2001, 156-164, vol. 36.

Wright K. et al., "Differential Expression of Cannabinoid Receptors in the Human Colon: Cannabinoids Promote Epithelial Wound Healing," Gastroenterology, 2005, 437-453, vol. 129.

Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.

Yoshihara S. et al., "Endogenous Cannabinoid Receptor Agonists Inhibit Neurogenic Inflammations in Guinea Pig Airways" Allergy and Immunology, 2005, 80-87, vol. 138.

Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.

Zimmer, A et al., "Increased mortality, hypoactivity, and hypoalgesia in cannabinoid CB1 receptor knockout mice," Proceedings of the National Academy of Science, 1999, 5780-5785, vol. 96.

COMPOUNDS AS CANNABINOID RECEPTOR LIGANDS

This application claims priority to U.S. Patent Application Ser. No. 60/841,666 filed Aug. 31, 2006 and is incorporated herein by reference.

TECHNICAL FIELD

The present invention relates to thiophene containing compounds, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY

The present invention generally provides thiophene containing compounds and pharmaceutical compositions and methods for the treatment of disorders using these compounds and pharmaceutical compositions.

In one embodiment, the present invention provides compounds of Formula (I),

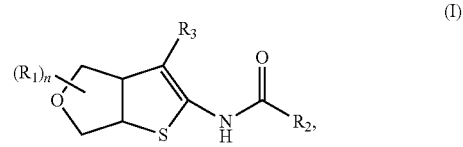

or a pharmaceutically suitable salt or prodrug thereof, wherein n is 0, 1, 2, 3, or 4;

$R_1$, at each occurrence, is independently selected from the group consisting of alkyl, alkoxylalkyl, haloalkyl, hydroxyalkyl, oxo, $R_4O_2C$—, $R_cR_dNC(O)$—, and $R_cR_dNS(O)_2$—; two $R_1$ together with the same carbon atom to which they are attached, optionally form a 4-, 5-, or 6-membered monocyclic cycloalkyl;

$R_2$ is selected from the group consisting of aryl, cycloalkyl, heterocycle, and $R_eR_fN$—;

$R_3$ is selected from the group consisting of alkyl, alkoxyalkyl, haloalkyl, hydroxyalkyl, $R_5$—C(O)—, $R_5$—C(=N—$OR_p$)—, $R_6OC(O)$—, $R_gR_jNC(O)$—, $R_5$—S(O)$_2$—, and $R_gR_jNS(O)_2$—;

$R_4$ is selected from the group consisting of alkyl, arylalkyl, haloalkyl, and heterocycloalkyl;

$R_5$, at each occurrence, is independently selected from the group consisting of alkyl, alkoxyalkyl, aryl, cycloalkyl, haloalkyl, heteroaryl, and heterocycle;

$R_6$ is selected from the group consisting of alkyl, arylalkyl, haloalkyl, cycloalkyl, cycloalkylalkyl, heterocycloalkyl, and heteroarylalkyl;

$R_c$ and $R_d$, at each occurrence, are each independently selected from the group consisting of hydrogen, alkyl, and haloalkyl, or $R_c$ and $R_d$ together with the nitrogen atom to which they are attached form a heterocyclic ring;

$R_e$ is selected from the group consisting of hydrogen, alkyl, haloalkyl, cycloalkylalkyl, and alkylcarbonyl;

$R_f$ is selected from the group consisting of hydrogen, alkyl, and haloalkyl;

$R_g$, at each occurrence, is independently selected from the group consisting of alkyl, alkenyl, alkynyl, cycloalkyl, hydroxyalkyl, alkoxyalkyl, arylalkyl, cycloalkylalkyl, haloalkyl, heteroarylalkyl, and heterocycloalkyl;

$R_j$, at each occurrence, is independently selected from the group consisting of hydrogen, alkyl, and haloalkyl; and $R_p$ is selected from the group consisting of hydrogen and alkyl.

In another embodiment, the present invention is a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

In yet another embodiment, the present invention is a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Another embodiment of the present invention relates to a method for providing neuroprotection in a mammal in need of such treatment. This method comprises administering to the mammal a therapeutically effective amount of a compound of formula (I) or a pharmaceutically acceptable salt thereof.

In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of a compound of formula (I) or a pharmaceutically acceptable salt thereof, in the manufacture of a medicament for the treatment of the disease conditions described above.

These and other objects of the invention are described in the following paragraphs. These objects should not be deemed to narrow the scope of the invention.

DEFINITION OF TERMS

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated from a reaction mixture.

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, 3-methoxypropyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein.

The term "alkyl" as used herein, means a saturated, straight or branched chain hydrocarbon containing from 1 to 10 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a saturated, straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkylene group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, and tetrahydrophenanthrenyl. The aryl groups of the present invention are attached to the parent molecular moiety through any substitutable atoms within the groups, and can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic hydrocarbon ring system. The monocyclic cycloalkenyl ring contains from 3 to 10 carbons and zero heteroatom in the ring. The 3, 4, and 5-membered ring contain one carbon-carbon double bond in the ring. The 6-membered ring contains one or two double bonds in the ring. The 7-10 membered rings contain one, two or three double bonds in the ring. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused with a monocyclic cycloalkyl or a monocyclic cycloalkenyl fused to a monocyclic cycloalkenyl. Representative examples of bicyclic cycloalkenyls include, but are not limited to, 3a,4,5,6,7,7a-hexahydro-1H-indenyl, and 1,2,3,4,5,6-hexahydro-pentalenyl. The cycloalkenyl groups of the present invention are attached to the parent molecular moiety through any substitutable carbon atoms within the groups, and are optionally substituted.

The term "cycloalkyl" as used herein, means a monocyclic cycloalkyl, or a bicyclic cycloalkyl. Monocyclic cycloalkyls are exemplified by a saturated cyclic hydrocarbon group containing from 3 to 8 carbon atoms. Bicyclic cycloalkyls are exemplified by a monocyclic cycloalkyl fused to a monocyclic cycloalkyl. The cycloalkyl groups of the present invention are appended to the parent molecular moiety through any substitutable carbon atom within the groups, and may contain one or two alkylene bridges of 1, 2, 3, or 4 carbon atoms wherein each bridge links two non-adjacent carbon atoms within the groups. Representative examples cycloalkyl groups include, but are not limited to, cyclopropyl, cyclobutyl, cyclopentyl, cyclohexyl, cycloheptyl, cyclooctyl, adamantyl(tricyclo[3.3.1.1$^{3,7}$]decyl), noradamantyl(octahydro-2,5-methanopentalene), bicyclo[2.2.2]octyl, bicyclo[3.3.1] nonyl, bicyclo[2.2.1]heptyl, and bicyclo[3.1.1]heptyl.

The term "cycloalkylalkyl" as used herein, means a cycloalkyl group appended to the parent molecular moiety through an alkylene group, as defined herein. Examples of cycloalkylalkyl include, but are not limited to, cyclopropylmethyl and cyclopropyl-1-methylethyl.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkylene group, as defined herein.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2,2-trifluoroethyl, trifluoromethyl, 3,3,3-trifluoropropyl, pentafluoroethyl, and 2-chloro-3-fluoropentyl.

The term "heteroaryl" as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three or four heteroatoms in the ring. The 6-membered ring contains three double bonds and one, two, three or four heteroatoms in the ring. Representative examples of monocyclic heteroaryls include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryls are exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothiophenyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl. The heteroaryl groups of the present invention are appended to the parent molecular moiety through a substitutable atom within the groups.

The term "heteroarylalkyl" as used herein, means a heteroaryl group appended to the parent molecular moiety through an alkylene group, as defined herein.

The term "heterocycle" or "heterocyclic" as used herein, means a monocyclic heterocycle, a bicyclic heterocycle, or a tricyclic heterocycle containing at least one heteroatom in the ring. The monocyclic heterocycle is a 3-, 4-, 5-, 6-, 7, or 8-membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6-, 7-, or 8-membered ring contains zero, one or two double bonds and one, two or three heteroatoms selected from the group consisting of O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycles of the present invention are exemplified by a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Representative examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The tricyclic heterocycle is a bicyclic heterocycle fused to a phenyl, or a bicyclic heterocycle fused to a monocyclic cycloalkyl, or a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. The heterocycle groups of the present invention are connected to the parent molecular moiety through any substitutable carbon atom or any substitutable nitrogen atom contained within the groups, and may contain one or two alkylene bridges of 1, 2, 3, or 4 carbon atoms, each linking two non-adjacent carbon atoms of the groups. Examples of such bridged heterocycle groups include, but are not limited to, oxatricyclo[3.3.1.1$^{3,7}$]decyl (including 2-oxatricyclo[3.3.1.1$^{3,7}$]decyl), 2,4-dioxabicyclo[4.2.1]nonyl, and oxabicyclo[2.2.1]heptyl (including 2-oxabicyclo[2.2.1]heptyl).

The term "heterocycloalkyl" as used herein, means a heterocycle group appended to the parent molecular moiety through an alkylene group, as defined herein. Non-limiting example of heterocycloalkyl includes tetrahydrofuranylmethyl.

The aryl, cycloalkyl, cycloalkenyl, heterocycle, and the heteroaryl groups of the present invention, as substituents or parts of the substituents, are each independently unsubstituted or substituted with 1, 2, 3, 4, 5 or 6 substituents, $R_{101}$, unless otherwise noted. Each $R_{101}$ is independently selected from the group consisting of alkenyl, alkoxy, alkoxyalkoxy, alkoxyalkoxyalkyl, alkoxyalkyl, alkoxycarbonyl, alkoxycarbonylalkyl, alkylsulfinyl, alkylsulfinylalkyl, alkoxysulfonyl, alkyl, alkylcarbonyl, alkylcarbonylalkyl, alkylcarbonyloxy, alkylsulfonyl, alkylsulfonylalkyl, alkylthio, alkylthioalkyl, alkynyl, carboxy, carboxyalkyl, cyano, cyanoalkyl, formyl, haloalkoxy, haloalkoxyalkyl, haloalkyl, halogen, hydroxy, hydroxyalkyl, mercapto, nitro, oxo, —$NZ_1Z_2$, and $(NZ_3Z_4)$carbonyl.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 2-hydroxypropyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "$NZ_1Z_2$" as used herein, means two groups, $Z_1$ and $Z_2$, which are appended to the parent molecular moiety through a nitrogen atom. $Z_1$ and $Z_2$ are each independently hydrogen, alkyl, alkylcarbonyl, aryl, arylalkyl and formyl. In certain instances within the present invention, $Z_1$ and $Z_2$ taken together with the nitrogen atom to which they are attached form a heterocyclic ring. Representative examples of $NZ_1Z_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently hydrogen, alkyl, aryl and arylalkyl. Representative examples of NZ$_3$Z$_4$ include, but are not limited to, amino, methylamino, phenylamino and benzylamino.

The term "(NZ$_3$Z$_4$)carbonyl" as used herein, means a NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

It is to be understood that both the foregoing general description and the following detailed description are exemplary, but are not restrictive, of the invention.

DETAILED DESCRIPTION

Compounds of the invention have the formula (I) as described above.

Examples of a group of compounds of formula (I) include those wherein R$_3$ is selected from the group consisting of alkyl, alkoxyalkyl, haloalkyl and hydroxyalkyl.

Other examples of a group of compounds of formula (I) include those wherein R$_3$ is R$_5$—C(O)— and R$_5$ is as defined in the summary section. For example, R$_5$ is cycloalkyl (such as, but not limited to, cyclopropyl, cyclobutyl, and cyclopentyl), heteroaryl (such as, but not limited to, furanyl), heterocycle (such as, but not limited to, aziridinyl and tetrahydropyranyl), or phenyl. Each of the rings as represented by R$_5$ is optional substituted as described in the Definition of Terms. Examples of the optional substituents of R$_5$ include, but are not limited to, alkyl, halogen, haloalkyl, hydroxy, and alkoxy.

Yet other examples of a group of compounds of formula (I) include those wherein R$_3$ is R$_6$OC(O)— and R$_6$ is as defined in the summary section. For example, R$_6$ is C$_{1-6}$ alkyl. In one embodiment R$_6$ is C$_{1-3}$ alkyl. In yet another embodiment, R$_6$ is ethyl or n-propyl.

Further examples of a group of compounds of formula (I) include those wherein R$_3$ is R$_5$—C(=N—OR$_p$)—, and R$_5$ and R$_p$ are as disclosed in the summary.

Yet further examples of a group include compounds of formula (I) wherein R$_3$ is R$_5$—S(O)$_2$— or R$_g$R$_j$NS(O)$_2$—, and R$_5$, R$_g$, and R$_j$ are as defined in the summary section.

Yet other examples of a group include compounds of formula (I) wherein R$_3$ is R$_g$R$_j$NC(O)—; and R$_g$ and R$_j$ are as disclosed in the summary section. For example, R$_g$ is alkyl (e.g. ethyl, n-propyl, isopropyl, isobutyl, and the like), alkynyl such as prop-2-ynyl, alkoxyalkyl (e.g. 2-methoxyethyl, etc.), hydroxyalkyl (e.g. 2-hydroxypropyl, 2-hydroxyethyl, 3-hydroxypropyl, etc.), haloalkyl (e.g. 3,3,3-trifluoropropyl, etc.), cycloalkyl (e.g. cyclopropyl, cyclobutyl, cyclopentyl, etc.), cycloalkylalkyl (e.g. cyclopropylmethyl, etc.), or heterocycloalkyl (e.g. tetrahydrofuranylmethyl, etc.), wherein the cycloalkyl, cycloalkyl moiety of cycloalkylalkyl, and the heterocycle moiety of heterocycloalkyl are each independently unsubstituted or substituted as described in the Definition of Terms. R$_j$, for example, is hydrogen.

Within each group of compounds of formula (I) as described in the preceding paragraphs, R$_2$, R$_1$ and n have values as defined in the Summary.

Thus, of each group of compounds of formula (I) as described in the preceding paragraphs, examples of a subgroup include those wherein R$_2$ is aryl, unsubstituted or substituted as described in the Definition of Terms. For example, R$_2$ is unsubstituted or substituted phenyl. Examples of the optional substituents include, but are not limited to, alkyl, haloalkyl, alkoxy, haloalkoxy, and halogen.

Other examples of a subgroup include those wherein R$_2$ is cycloalkyl, unsubstituted or substituted as described in the Definition of Terms. For example, R$_2$ is cyclopropyl, bicyclo[2.2.2]octyl, bicyclo[2.2.1]heptyl, or octahydro-2,5-methanopentalene, each of which is optionally substituted. Examples of the optional substituents include, but are not limited to, alkyl, alkoxy, and oxo.

Further examples of a subgroup include those wherein R$_2$ is heterocycle, unsubstituted or substituted as described in the Definition of Terms. For example, R$_2$ is dihydropyranyl, oxabicyclo[2.2.1]heptyl, or oxatricylo[3.3.1.1$^{3,7}$]decyl, each of which is optionally substituted. Examples of the optional substituents include, but are not limited to, alkyl, alkoxy, and oxo.

Yet other examples of a subgroup include those wherein R$_2$ is R$_e$R$_f$N— and R$_e$ and R$_f$ are as described in the Summary. For example, R$_e$ is cycloalkylalkyl such as, but not limited to, cyclopropyl-1-methylethyl, wherein the cycloalkyl moiety is optionally substituted as described in the Definition of Terms. R$_f$, for example, is hydrogen.

Of all examples of the groups and subgroups of compounds of formula (I) as discussed herein-above, R$_1$ and n have the meanings as described in the Summary. For example, one embodiment is directed to the above mentioned groups and sub-groups wherein R$_1$ is C$_{1-6}$ alkyl, and n is 1, 2, 3, or 4. For example, R$_1$ is methyl.

Exemplary compounds of the invention include, but are not limited to compounds of formula (I):

ethyl 2-{[2-fluoro-6-(trifluoromethyl)benzoyl]amino}-4-methyl-4,6-dihydrothieno[2,3-c]furan-3-carboxylate;

N-{3-[(3,3-difluoroazetidin-1-yl)carbonyl]-4-methyl-4,6-dihydrothieno[2,3-c]furan-2-yl}-2-fluoro-6-(trifluoromethyl)benzamide;

ethyl 4-methyl-2-{[2-(trifluoromethyl)benzoyl]amino}-4,6-dihydrothieno[2,3-c]furan-3-carboxylate;

N-[3-(azetidin-1-ylcarbonyl)-4-methyl-4,6-dihydrothieno[2,3-c]furan-2-yl]-2-fluoro-6-(trifluoromethyl)benzamide;

N-{3-[(3,3-difluoroazetidin-1-yl)carbonyl]-4-methyl-4,6-dihydrothieno[2,3-c]furan-2-yl}-2-(trifluoromethyl)benzamide;

ethyl 2-{[3-chloro-2-fluoro-6-(trifluoromethyl)benzoyl]amino}-4-methyl-4,6-dihydrothieno[2,3-c]furan-3-carboxylate;

2-fluoro-N-{3-[(3-methoxyazetidin-1-yl)carbonyl]-4-methyl-4,6-dihydrothieno[2,3-c]furan-2-yl}-6-(trifluoromethyl)benzamide;

N-(3-benzoyl-4-methyl-4,6-dihydrothieno[2,3-c]furan-2-yl)-2-fluoro-6-(trifluoromethyl)benzamide;

N-[3-(cyclobutylcarbonyl)-4-methyl-4,6-dihydrothieno[2,3-c]furan-2-yl]-2-fluoro-6-(trifluoromethyl)benzamide;

N-[3-(cyclopropylcarbonyl)-4-methyl-4,6-dihydrothieno[2,3-c]furan-2-yl]-2-fluoro-6-(trifluoromethyl)benzamide;

N-[3-(cyclopentylcarbonyl)-4-methyl-4,6-dihydrothieno[2,3-c]furan-2-yl]-2-fluoro-6-(trifluoromethyl)benzamide;

2-chloro-N-[3-(cyclobutylcarbonyl)-4-methyl-4,6-dihydrothieno[2,3-c]furan-2-yl]-6-fluorobenzamide;

N-(3-benzoyl-4-methyl-4,6-dihydrothieno[2,3-c]furan-2-yl)-3-chloro-2-fluoro-6-(trifluoromethyl)benzamide;

N-[3-(cyclobutylcarbonyl)-4-methyl-4,6-dihydrothieno[2,3-c]furan-2-yl]-N'-(1-cyclopropyl-1-methylethyl)urea;
ethyl 2-[(2,6-difluorobenzoyl)amino]-4-methyl-4,6-dihydrothieno[2,3-c]furan-3-carboxylate;
2-fluoro-N-[3-(2-furoyl)-4-methyl-4,6-dihydrothieno[2,3-c]furan-2-yl]-6-(trifluoromethyl)benzamide;
ethyl 2-[(2-chloro-6-fluorobenzoyl)amino]-4-methyl-4,6-dihydrothieno[2,3-c]furan-3-carboxylate;
ethyl 2-{[2-fluoro-6-(trifluoromethyl)benzoyl]amino}-4,4,6,6-tetramethyl-4,6-dihydrothieno[2,3-c]furan-3-carboxylate;
ethyl 2-{[5-chloro-2-(trifluoromethyl)benzoyl]amino}-4,4,6,6-tetramethyl-4,6-dihydrothieno[2,3-c]furan-3-carboxylate;
ethyl 4,4,6,6-tetramethyl-2-{[(2,2,3,3-tetramethylcyclopropyl)carbonyl]amino}-4,6-dihydrothieno[2,3-c]furan-3-carboxylate;
ethyl 2-{[(1-methoxybicyclo[2.2.2]oct-2-yl)carbonyl]amino}-4,4,6,6-tetramethyl-4,6-dihydrothieno[2,3-c]furan-3-carboxylate;
ethyl 4,4,6,6-tetramethyl-2-({[(1S,2R,4R)-2-methylbicyclo[2.2.1]hept-2-yl]carbonyl}amino)-4,6-dihydrothieno[2,3-c]furan-3-carboxylate;
4,4,6,6-tetramethyl-N-propyl-2-{[(2,2,3,3-tetramethylcyclopropyl)carbonyl]amino}-4,6-dihydrothieno[2,3-c]furan-3-carboxamide;
ethyl 4-methyl-2-{[(2,2,3,3-tetramethylcyclopropyl)carbonyl]amino}-4,6-dihydrothieno[2,3-c]furan-3-carboxylate;
ethyl 4-methyl-2-({[(1S,2R,4R)-2-methylbicyclo[2.2.1]hept-2-yl]carbonyl}amino)-4,6-dihydrothieno[2,3-c]furan-3-carboxylate;
N-{3-[(3,3-difluoroazetidin-1-yl)carbonyl]-4-methyl-4,6-dihydrothieno[2,3-c]furan-2-yl}-2,2,3,3-tetramethylcyclopropanecarboxamide;
5-chloro-N-{3-[(3,3-difluoroazetidin-1-yl)carbonyl]-4-methyl-4,6-dihydrothieno[2,3-c]furan-2-yl}-2-methoxybenzamide;
2-fluoro-N-{3-[(3-hydroxyazetidin-1-yl)carbonyl]-4-methyl-4,6-dihydrothieno[2,3-c]furan-2-yl}-6-(trifluoromethyl)benzamide;
N-(3-benzoyl-4-methyl-4,6-dihydrothieno[2,3-c]furan-2-yl)-2,2,3,3-tetramethylcyclopropanecarboxamide;
N-[3-(cyclobutylcarbonyl)-4-methyl-4,6-dihydrothieno[2,3-c]furan-2-yl]-2,2,3,3-tetramethylcyclopropanecarboxamide;
N-[3-(cyclobutylcarbonyl)-4-methyl-4,6-dihydrothieno[2,3-c]furan-2-yl]hexahydro-2,5-methanopentalene-3a(1H)-carboxamide;
N-[3-(cyclopropylcarbonyl)-4-methyl-4,6-dihydrothieno[2,3-c]furan-2-yl]hexahydro-2,5-methanopentalene-3a(1H)-carboxamide;
N-[3-(cyclopentylcarbonyl)-4-methyl-4,6-dihydrothieno[2,3-c]furan-2-yl]hexahydro-2,5-methanopentalene-3a(1H)-carboxamide;
N-[3-(2-furoyl)-4-methyl-4,6-dihydrothieno[2,3-c]furan-2-yl]hexahydro-2,5-methanopentalene-3a(1H)-carboxamide;
N-[3-(cyclobutylcarbonyl)-4-methyl-4,6-dihydrothieno[2,3-c]furan-2-yl]-2,2-dimethyl-4-oxo-3,4-dihydro-2H-pyran-6-carboxamide;
N-[3-(cyclobutylcarbonyl)-4-methyl-4,6-dihydrothieno[2,3-c]furan-2-yl]-2-ethoxybenzamide;
2-chloro-N-[3-(cyclobutylcarbonyl)-4-methyl-4,6-dihydrothieno[2,3-c]furan-2-yl]-5-fluorobenzamide;
N-[3-(cyclobutylcarbonyl)-4-methyl-4,6-dihydrothieno[2,3-c]furan-2-yl]-2-(trifluoromethoxy)benzamide;
ethyl 2-[(2,6-dichlorobenzoyl)amino]-4-methyl-4,6-dihydrothieno[2,3-c]furan-3-carboxylate;
ethyl 4-methyl-2-{[2-oxatricyclo[3.3.1.1~3,7~]dec-1-ylcarbonyl]amino}-4,6-dihydrothieno[2,3-c]furan-3-carboxylate;
N-{3-[(3,3-difluoroazetidin-1-yl)carbonyl]-4-methyl-4,6-dihydrothieno[2,3-c]furan-2-yl}-2-oxatricyclo[3.3.1.1~3,7~]decane-1-carboxamide;
N-{3-[(3,3-difluoroazetidin-1-yl)carbonyl]-4-methyl-4,6-dihydrothieno[2,3-c]furan-2-yl}hexahydro-2,5-methanopentalene-3a(1H)-carboxamide;
2-{[2-fluoro-6-(trifluoromethyl)benzoyl]amino}-4,4,6,6-tetramethyl-N-propyl-4,6-dihydrothieno[2,3-c]furan-3-carboxamide;
2-{[2-fluoro-6-(trifluoromethyl)benzoyl]amino}-N-(2-methoxyethyl)-4,4,6,6-tetramethyl-4,6-dihydrothieno[2,3-c]furan-3-carboxamide;
ethyl 4-methyl-2-({[(1S,4R)-4,7,7-trimethyl-3-oxo-2-oxabicyclo[2.2.1]hept-1-yl]carbonyl}amino)-4,6-dihydrothieno[2,3-c]furan-3-carboxylate;
(1S,4R)—N-{3-[(3,3-difluoroazetidin-1-yl)carbonyl]-4-methyl-4,6-dihydrothieno[2,3-c]furan-2-yl}-4,7,7-trimethyl-3-oxo-2-oxabicyclo[2.2.1]heptane-1-carboxamide;
ethyl 2-{[5-chloro-2-(trifluoromethyl)benzoyl]amino}-4-methyl-4,6-dihydrothieno[2,3-c]furan-3-carboxylate;
3-chloro-N-{3-[(3,3-difluoroazetidin-1-yl)carbonyl]-4-methyl-4,6-dihydrothieno[2,3-c]furan-2-yl}-2-fluoro-6-(trifluoromethyl)benzamide;
3-chloro-2-fluoro-N-{3-[(3-methoxyazetidin-1-yl)carbonyl]-4-methyl-4,6-dihydrothieno[2,3-c]furan-2-yl}-6-(trifluoromethyl)benzamide;
2-fluoro-N-[4-methyl-3-(tetrahydro-2H-pyran-4-ylcarbonyl)-4,6-dihydrothieno[2,3-c]furan-2-yl]-6-(trifluoromethyl)benzamide;
5-chloro-N-{3-[(3,3-difluoroazetidin-1-yl)carbonyl]-4-methyl-4,6-dihydrothieno[2,3-c]furan-2-yl}-2-(trifluoromethyl)benzamide;
ethyl 2-[(2,6-dimethylbenzoyl)amino]-4-methyl-4,6-dihydrothieno[2,3-c]furan-3-carboxylate;
2-{[2-fluoro-6-(trifluoromethyl)benzoyl]amino}-4,4,6,6-tetramethyl-N-(3,3,3-trifluoropropyl)-4,6-dihydrothieno[2,3-c]furan-3-carboxamide;
N-cyclobutyl-2-{[2-fluoro-6-(trifluoromethyl)benzoyl]amino}-4,4,6,6-tetramethyl-4,6-dihydrothieno[2,3-c]furan-3-carboxamide;
N-cyclopentyl-2-{[2-fluoro-6-(trifluoromethyl)benzoyl]amino}-4,4,6,6-tetramethyl-4,6-dihydrothieno[2,3-c]furan-3-carboxamide;
2-{[2-fluoro-6-(trifluoromethyl)benzoyl]amino}-N-isobutyl-4,4,6,6-tetramethyl-4,6-dihydrothieno[2,3-c]furan-3-carboxamide;
2-{[2-fluoro-6-(trifluoromethyl)benzoyl]amino}-4,4,6,6-tetramethyl-N-[(2S)-tetrahydrofuran-2-ylmethyl]-4,6-dihydrothieno[2,3-c]furan-3-carboxamide;
N-(cyclopropylmethyl)-2-{[2-fluoro-6-(trifluoromethyl)benzoyl]amino}-4,4,6,6-tetramethyl-4,6-dihydrothieno[2,3-c]furan-3-carboxamide;
2-{[2-fluoro-6-(trifluoromethyl)benzoyl]amino}-4,4,6,6-tetramethyl-N-[(2R)-tetrahydrofuran-2-ylmethyl]-4,6-dihydrothieno[2,3-c]furan-3-carboxamide;
propyl 4,4,6,6-tetramethyl-2-{[2-(trifluoromethyl)benzoyl]amino}-4,6-dihydrothieno[2,3-c]furan-3-carboxylate;
propyl 2-{[2-fluoro-6-(trifluoromethyl)benzoyl]amino}-4,4,6,6-tetramethyl-4,6-dihydrothieno[2,3-c]furan-3-carboxylate;

2-{[2-fluoro-6-(trifluoromethyl)benzoyl]amino}-N-isopropyl-4,4,6,6-tetramethyl-4,6-dihydrothieno[2,3-c]furan-3-carboxamide;

2-{[2-fluoro-6-(trifluoromethyl)benzoyl]amino}-4,4,6,6-tetramethyl-N-prop-2-ynyl-4,6-dihydrothieno[2,3-c]furan-3-carboxamide;

2-{[2-fluoro-6-(trifluoromethyl)benzoyl]amino}-N-[(2S)-2-hydroxypropyl]-4,4,6,6-tetramethyl-4,6-dihydrothieno[2,3-c]furan-3-carboxamide;

ethyl 2-{[4-fluoro-2-(trifluoromethyl)benzoyl]amino}-4,4,6,6-tetramethyl-4,6-dihydrothieno[2,3-c]furan-3-carboxylate;

ethyl 2-{[5-fluoro-2-(trifluoromethyl)benzoyl]amino}-4,4,6,6-tetramethyl-4,6-dihydrothieno[2,3-c]furan-3-carboxylate;

2-{[2-fluoro-6-(trifluoromethyl)benzoyl]amino}-N-(2-hydroxyethyl)-4,4,6,6-tetramethyl-4,6-dihydrothieno[2,3-c]furan-3-carboxamide; and 2-{[2-fluoro-6-(trifluoromethyl)benzoyl]amino}-N-(3-hydroxypropyl)-4,4,6,6-tetramethyl-4,6-dihydrothieno[2,3-c]furan-3-carboxamide.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Preparation of Compounds a. ABBREVIATIONS

Abbreviations which have been used in the descriptions of the Schemes and the Examples that follow are: DMSO for dimethyl sulfonamide and THF for tetrahydrofuran.

b. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R_e$, $R_f$, $R_g$, $R_j$, $R_1$, $R_2$, $R_3$, $R_5$, $R_6$, and n have the meanings as set forth in the summary section unless otherwise noted, can be synthesized as shown in Schemes 1-7.

Scheme 1

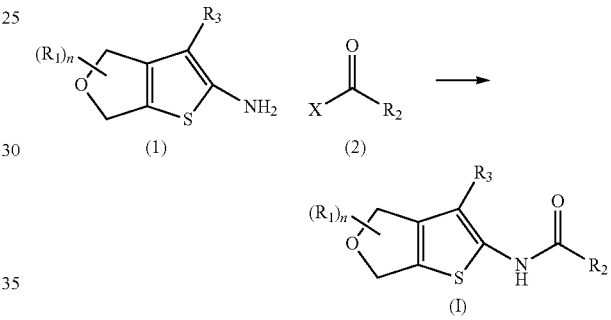

As shown in Scheme 1, compounds of formula (I) can be prepared by treating compounds of formula (1) with compounds of formula (2) wherein X is chloro or —OH under appropriate conditions. For example, compounds of formula (I) can be obtained by stirring an about equimolar mixture of the compounds of formula (2) wherein X is chloro, and compounds of formula (1) in solvents such as chloroform, dichloromethane or tetrahydrofuran, in the presence of a base such as, but not limited to, diisopropylethylamine and at a temperature of about 0° C. to about 40° C. Alternatively, compounds of formula (I) can be prepared by stirring an equimolar mixture of compounds of formula (2) wherein X is —OH and compounds of formula (1), a coupling reagent, optionally a coupling auxiliary, and optionally a base, in a solvent such as, but not limited to, tetrahydrofuran, N,N-dimethylacetamide, N,N-dimethylformamide, dichloromethane, ethyl acetate, or mixtures thereof. Non-limiting examples of coupling reagents are 1,1'-carbonyldiimidazole (CDI), bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), and O-benzotriazol-1-yl-N,N,N',N'-tetramethyluronium tetrafluoroborate (TBTU). Non-limiting examples of coupling auxiliary are 1-hydroxy-7-azabenzotriazole (HOAT) and 1-hydroxybenzotriazole hydrate (HOBT). Examples of suitable base include, but are not limited to N-methyl morpholine, diisopropylethylamine, pyridine, and the like. The coupling reactions can be carried out, for example, at a temperature between about 0° C. to about 65° C., and optionally in a microwave reactor.

Compounds of formula (I) wherein $R_2$ is $R_eR_fN$— can be prepared using general procedures as outlined in Schemes 2-4.

Scheme 2

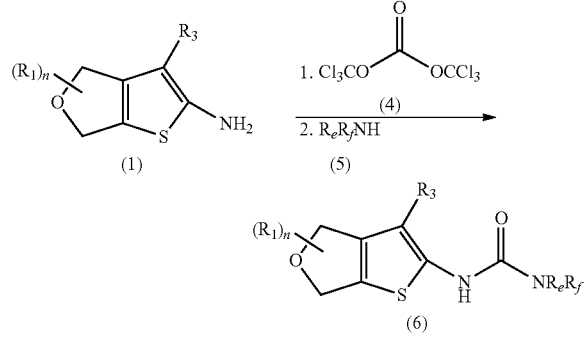

Compounds of formula (1) when treated with triphosgene of formula (4) in the presence of a base, followed by addition of an amine of formula (5) provide compounds of formula (6). Examples of suitable bases include, but are not limited to, triethylamine and diisopropylethylamine.

Scheme 3

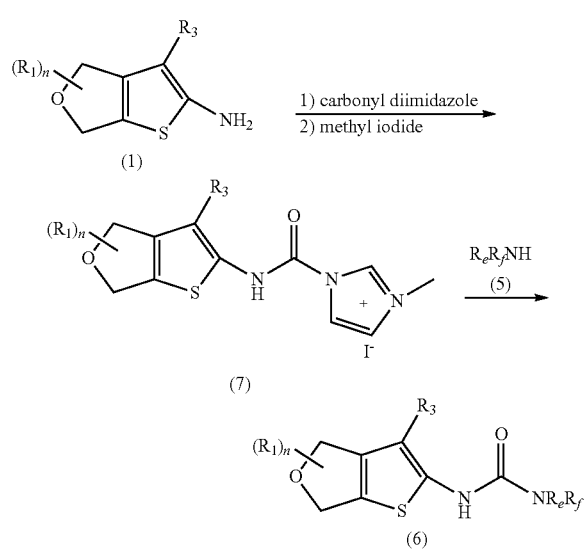

Compounds of formula (6) can be prepared from compounds of formula (1) by (a) treating with 1,1'-carbonyldiimidazole, followed by treatment with methyl iodide, and (b) treating the product from step (a) with an amine of formula (5).

Scheme 4

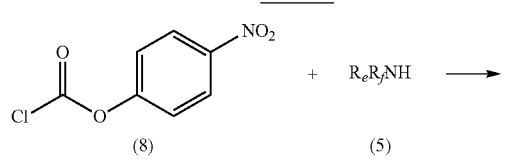

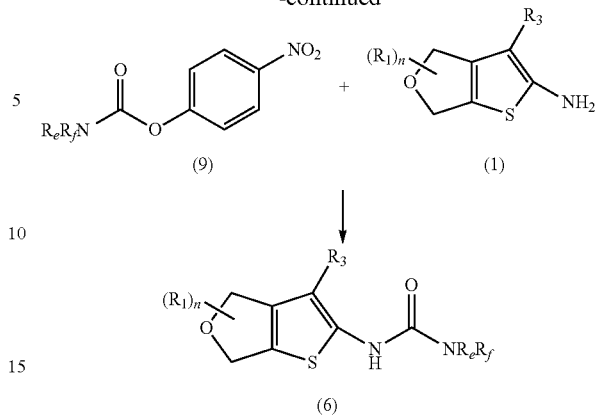

Compounds of formula (6) can also be obtained from (a) reacting compounds of formula (8) with an amine of formula (5), and (b) treating product from step (a) with compounds of formula (1).

Compounds of formula (I) wherein $R_2$ is $NR_eR_f$ and $R_f$ is hydrogen can be synthesized using general procedures as shown in Scheme 5.

Scheme 5

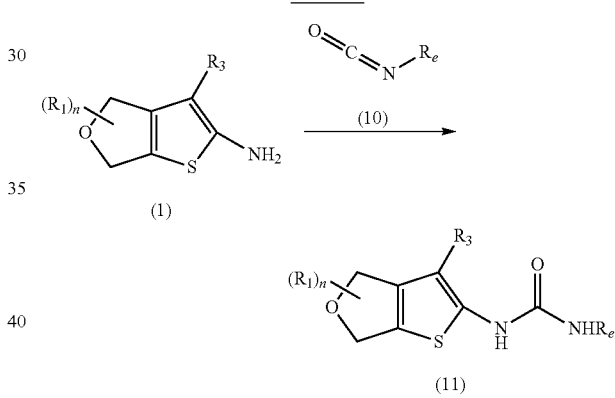

Compounds of formula (1) when treated with an isocyanate of formula (10) provide compounds of formula (11).

Scheme 6

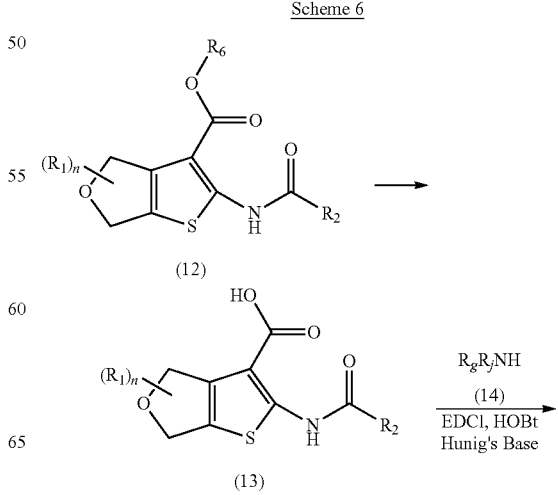

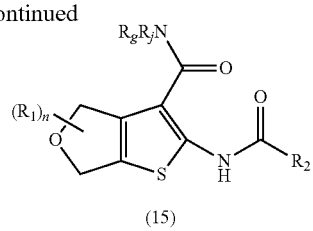

(15)

As outlined in Scheme 6, compounds of formula (12) can be hydrolyzed to the corresponding carboxylic acids of formula (13) using reaction conditions known to one skilled in the art. For example, treatment of compounds of formula (12) with sodium, lithium or potassium hydroxide in an aqueous alcoholic solvent such as but not limited to aqueous methanol or ethanol, provide acids of formula (13). Reaction of compounds of formula (13) with amines of formula (14) can be achieved by using reaction conditions as described in Scheme 1.

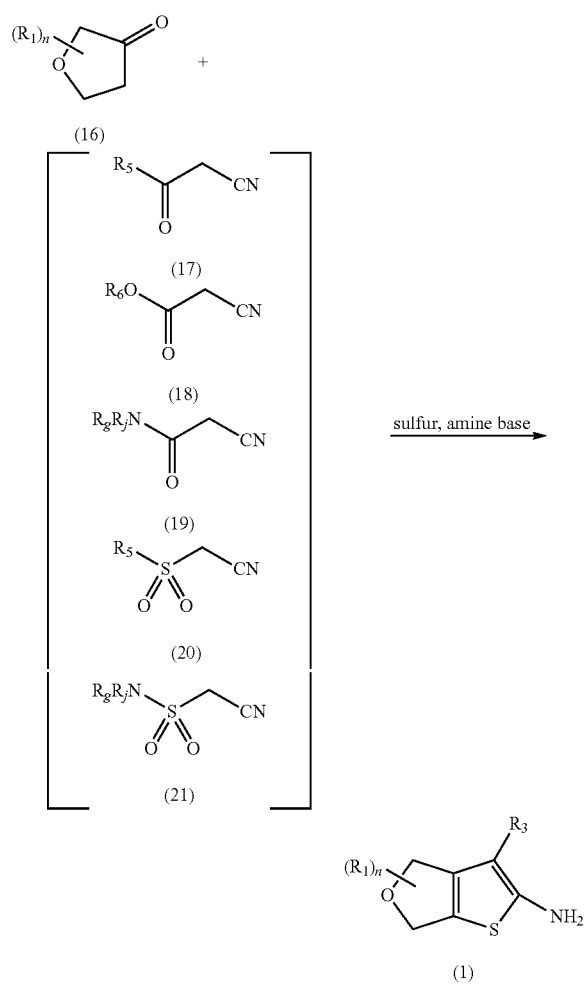

As shown in Scheme 7, compounds of formula (1) wherein $R_3$ is $R_5C(O)—$, $R_6O—C(O)—$, $R_gR_jNC(O)—$, $R_5S(O)_2—$ or $R_gR_jNS(O)_2—$, respectively, can be prepared from a Gewald reaction involving the condensation of compounds of formula (16) with compounds of formula (17), (18), (19), (20) or (21), and elemental sulfur, in the presence of about 0.5 to about 1 equivalent of an amine base. The Gewald reaction is typically carried out in a solvent such as, but are not limited to, ethanol, N,N-dimethylformamide or dioxane, at ambient or at elevated temperature. Suitable examples of the amines include, but are not limited to, diethylamine, morpholine or triethylamine. A further review of the chemistry describing the Gewald reaction can be found in *J. Heterocyclic Chem.*, 1999, 36, 333-345, Sabnis, R. W.; Rangnekar, D. W.; Sonawane, N. D.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geo- c. EXAMPLES

Example 1 ethyl 2-{[2-fluoro-6-(trifluoromethyl)benzoyl]
amino}-4-methyl-4,6-dihydrothieno[2,3-c]furan-3-
carboxylate

Example 1A 2-amino-4-methyl-4,6-dihydrothieno[2,3-c]furan-3-
carboxylic acid ethyl ester To a 500-mL, round-bottomed flask containing a magnetic stir bar were added 2-methyltetrahydro-furan-3-one (10.0 g, 100 mmol), ethyl cyanoacetate (12.4 g, 11.7 mL, 110 mmol), and sulfur powder (3.53 g, 110 mmol). The mixture was stirred to form a yellow slurry and morpholine (13.1 g, 13.1 mL, 150 mmol) was added. A reflux condenser with $N_2$ inlet was attached and a heating mantle was applied. The mixture was heated to 50-60° C. and stirred overnight. After cooling to room temperature, the volatiles were removed under reduced pressure. The residue was purified by flash chromatography (silica gel: 25% ethyl acetate in hexanes, $R_f$~0.3) to provide the title compound. $^1$H NMR (DMSO-$d_6$, 300 MHz) δ 1.24 (t, J=7.1 Hz, 3H), 1.33 (d, J=6.1 Hz, 3H), 4.06-4.25 (m, 2H), 4.68 (dd, J=10.8, 2.0 Hz, 1H), 4.82 (dd, J=10.8, 4.6 Hz, 1H), 5.05-5.15 (m, 1H), 7.34 (br s, 2H); MS (ESI$^+$) m/z 228 (M+H)$^+$. Anal. calcd. for $C_{20}H_{17}F_4NO_4S$: C, 54.17; H, 3.86; N, 3.16. Found: C, 54.17; H, 3.78; N, 3.13.

Example 1B ethyl 2-{[2-fluoro-6-(trifluoromethyl)benzoyl]
amino}-4-methyl-4,6-dihydrothieno[2,3-c]furan-3-
carboxylate To a 20-mL scintillation vial containing a magnetic stir bar were Example 1A (227 mg, 1.00 mmol), anhydrous tetrahydrofuran (8 mL), and triethylamine (455 mg, 627 mL, 4.50 mmol). A solution of 2-fluoro-6-trifluoromethylbenzoyl chloride (340 mg, 1.50 mmol) in a few drops of anhydrous tetrahydrofuran was added to the mixture. The mixture was stirred at room temperature for 24 hours. Saturated aqueous sodium bicarbonate solution (10 mL) was added and the resulting mixture was extracted with dichloromethane (3×10 mL). The combined organic extracts were dried over magnesium sulfate, filtered, and concentrated under reduced pressure. The residue was purified by flash chromatography (silica gel: 30% ethyl acetate in hexanes, $R_f$~0.3) to provide the title compound. $^1$H NMR (DMSO-$d_6$, 300 MHz) δ 1.27 (t, J=7.1 Hz, 3H), 1.40 (d, J=6.1 Hz, 3H), 4.17-4.34 (m, 2H), 4.89 (dd, J=11.5, 1.7 Hz, 1H), 5.03 (dd, J=11.7, 4.2 Hz, 1H), 5.25-5.34 (m, 1H), 7.67-7.89 (m, 3H), 11.51 (br s, 1H); MS (ESI$^+$) m/z 418 (M+H)$^+$.

Example 2

N-{3-[(3,3-difluoroazetidin-1-yl)carbonyl]-4-methyl-4,6-dihydrothieno[2,3-c]furan-2-yl}-2-fluoro-6-(trifluoromethyl)benzamide

Example 2A 2-(2-fluoro-6-trifluoromethyl-benzoylamino)-4-methyl-4,6-dihydro-thieno[2,3-c]furan-3-carboxylic acid A mixture of Example 1B (334 mg, 0.800 mmol) and solid potassium hydroxide (337 mg, 6.00 mmol) in ethanol (4 mL) and water (1 mL) were heated to reflux for 1 hour. After cooling to room temperature, 1 N aqueous HCl was added dropwise to adjust the mixture to pH 1. The mixture was extracted with ethyl acetate (3×10 mL). The combined extracts were dried over magnesium sulfate, filtered, and concentrated under reduced pressure to provide the title compound. LC-MS (ESI$^+$) m/z 390 (M+H)$^+$.

Example 2B

N-[3-(3,3-difluoroazetidine)-1-carbonyl)-4-methyl-4,6-dihydrothieno[2,3-c]furan-2-yl]-2-fluoro-6-trifluoromethylbenzamide To a 20-mL scintillation vial flask containing a magnetic stir bar were added Example 2A (97 mg, 0.25 mmol), 1-hydroxy-benzotriazole (51 mg, 0.38 mmol), and 3,3-difluoroazetidine hydrochloride (65 mg, 0.50 mmol). Anhydrous N,N-dimethylformide (2 mL) and diisopropylethylamine (65 mg, 87 μL, 0.50 mmol) were added. N-(3-Dimethylaminopropyl)-N'-ethylcarbodiimide hydrochloride (72 mg, 0.38 mmol) was added and the mixture stirred at room temperature overnight. The solvent/volatiles were removed under reduced pressure. The residue was purified by flash chromatography (silica gel: 30% ethyl acetate in hexanes) to provide the title compound. $^1$H NMR (DMSO-$d_6$, 300 MHz) δ 1.30 (d, J=6.4 Hz, 3H), 4.29-4.50 (m, 4H), 4.88-5.01 (m, 2H), 5.16-5.25 (m, 1H), 7.73-7.82 (m, 3H), 11.83 (br s, 1H); MS (ESI$^+$) m/z 465 (M+H)$^+$.

Example 3 ethyl 4-methyl-2-{[2-(trifluoromethyl)benzoyl]
amino}-4,6-dihydrothieno[2,3-c]furan-3-carboxylate The title compound was prepared according to the procedure outlined in Example 1B, substituting 2-trifluoromethylbenzoyl chloride for 2-fluoro-6-trifluoromethylbenzoyl chloride. $^1$H NMR (DMSO-$d_6$, 300 MHz) δ 1.28 (t, J=7.1 Hz, 3H), 1.41 (d, J=6.1 Hz, 3H), 4.18-4.36 (m, 2H), 4.90 (dd, J=11.8, 1.8 Hz, 1H), 5.03 (dd, J=11.9, 4.4 Hz, 1H), 5.28-5.34 (m, 1H), 7.79-7.95 (m, 4H), 11.29 (br s, 1H); MS (ESI$^+$) m/z 400 (M+H)$^+$. Anal. calcd. for $C_{18}H_{16}F_3NO_4S$: C, 54.13; H, 4.04; N, 3.51. Found: C, 53.63; H, 3.57; N, 3.37.

Example 4

N-[3-(azetidin-1-ylcarbonyl)-4-methyl-4,6-dihydrothieno[2,3-c]furan-2-yl]-2-fluoro-6-(trifluoromethyl)benzamide The title compound was prepared according to the procedure outlined in Example 2B, substituting azetidine hydrochloride for 3,3-difluoroazetidine hydrochloride. $^1$H NMR (DMSO-$d_6$, 300 MHz) δ 1.30 (d, J=6.1 Hz, 3H), 2.13-2.24 (m, 2H), 3.86-4.06 (m, 4H), 4.88-5.01 (m, 2H), 5.13-5.21 (m, 1H), 7.72-7.84 (m, 3H), 11.81 (br s, 1H). MS (ESI$^+$) m/z 429 (M+H)$^+$.

Example 5

N-[3-[(3,3-difluoroazetidin-1-yl)carbonyl]-4-methyl-4,6-dihydrothieno[2,3-c]furan-2-yl]-2-(trifluoromethyl)benzamide

Example 5A 4-methyl-2-(2-trifluoromethylbenzoylamino)-4,6-dihydrothieno[2,3-c]furan-3-carboxylic acid The title compound was prepared according to the procedure outlined in Example 2A, substituting Example 3 for Example 1B. LC-MS (ESI$^+$) m/z 372 (M+H)$^+$.

Example 5B

N-{3-[(3,3-difluoroazetidin-1-yl)carbonyl]-4-methyl-4,6-dihydrothieno[2,3-c]furan-2-yl}-2-(trifluoromethyl)benzamide The title compound was prepared according to the procedure outlined in Example 2B, substituting Example 5A for Example 2A. $^1$H NMR (DMSO-$d_6$, 300 MHz), 1.30 (d, J=6.4 Hz, 3H), 4.30-4.54 (m, 4H), 4.89-5.01 (m, 2H), 5.20-5.28 (m, 1H), 7.72-7.90 (m, 4H), 11.51 (br s, 1H). MS (ESI$^+$) m/z 447 (M+H)$^+$.

Example 6 ethyl 2-{[3-chloro-2-fluoro-6-(trifluoromethyl)benzoyl]amino}-4-methyl-4,6-dihydrothieno[2,3-c]furan-3-carboxylate The title compound was prepared according to the procedure outlined in Example 1B, substituting 3-chloro-2-fluoro-6-trifluoromethyl-benzoyl chloride for 2-fluoro-6-trifluoromethylbenzoyl chloride. $^1$H NMR (DMSO-$d_6$, 300 MHz) δ 1.27 (t, J=7.1 Hz, 3H), 1.40 (D, J=6.1 Hz, 3H), 4.20-4.32 (m, 2H), 4.89 (dd, J=11.8 2.0 Hz, 1H), 5.03 (dd, J=11.8, 4.4 Hz, 1H), 5.26-5.34 (m, 1H), 7.77 (d, J=8.8 Hz, 1H), 8.02 (dd, J=8.8, 8.0 Hz, 1H), 11.62 (br s, 1H). MS (ESI$^+$) m/z 452 (M+H)$^+$.

Example 7

2-fluoro-N-{3-[(3-methoxyazetidin-1-yl)carbonyl]-4-methyl-4,6-dihydrothieno[2,3-c]furan-2-yl}-6-(trifluoromethyl)benzamide The title compound was prepared according to the procedure outlined in Example 2B, substituting 3-methoxyazetidine hydrochloride for 3,3-difluoroazetidine hydrochloride. $^1$H NMR (DMSO-$d_6$, 300 MHz) δ 1.28 (d, J=6.4 Hz, 3H), 3.19 (s, 3H), 3.69-3.76 (m, 1H), 3.83-3.86 (m, 1H), 4.02-4.19 (m, 1H), 4.14-4.23 (m, 2H), 4.88-5.01 (m, 2H), 5.13-5.22 (m, 1H), 7.71-7.84 (m, 3H), 11.78 (br s, 1H). MS (ESI$^+$) m/z 452 (M+H)$^+$. Anal. calcd. for $C_{20}H_{18}F_4N_2O_4S$: C, 52.40; H, 3.96; N, 6.11. Found: C, 52.31; H, 3.74; N, 5.83.

Example 8

N-(3-benzoyl-4-methyl-4,6-dihydrothieno[2,3-c]furan-2-yl)-2-fluoro-6-(trifluoromethyl)benzamide

Example 8A (2-Amino-4-methyl-4,6-dihydrothieno[2,3-c]furan-3-yl)-phenylmethanone The title compound was prepared according to the procedure outlined in Example 1A substituting 3-oxo-3-phenyl-propionitrile for ethyl cyanoacetate. LC-MS (ESI$^+$) m/z 260 (M+H)$^+$.

Example 8B

N-(3-benzoyl-4-methyl-4,6-dihydrothieno[2,3-c]furan-2-yl)-2-fluoro-6-(trifluoromethyl)benzamide The title compound was prepared according to the procedure outlined in Example 1B, substituting Example 8A for Example 1A. $^1$H NMR (DMSO-$d_6$, 300 MHz) δ 0.82 (d, J=5.1 Hz, 3H), 4.95-4.99 (m, 3H), 7.51-7.56 (m, 2H), 7.64-7.78 (m, 6H), 11.86 (br s, 1H). MS (ESI$^+$) m/z 450 (M+H)$^+$. Anal. calcd. for $C_{22}H_{15}F_4NO_3S$: C, 58.80; H, 3.36; N, 3.12. Found: C, 58.54; H, 3.01; N, 3.07.

Example 9

N-[3-(cyclobutylcarbonyl)-4-methyl-4,6-dihydrothieno[2,3-c]furan-2-yl]-2-fluoro-6-(trifluoromethyl)benzamide

Example 9A (2-amino-4-methyl-4,6-dihydro-thieno[2,3-c]furan-3-yl)-cyclobutylmethanone The title compound was prepared according to the procedure outlined in Example 1A substituting 3-cyclobutyl-3-oxopropanenitrile for ethyl cyanoacetate. LC-MS (ESI$^+$) m/z 238 (M+H)$^+$.

Example 9B

N-[3-(cyclobutylcarbonyl)-4-methyl-4,6-dihydrothieno[2,3-c]furan-2-yl]-2-fluoro-6-(trifluoromethyl)benzamide The title compound was prepared according to the procedure outlined in Example 1B, substituting Example 9A for Example 1A. $^1$H NMR (CDCl$_3$, 300 MHz) δ 1.49 (d, J=6.4 Hz, 3H), 1.90-2.36 (m, 5H), 2.44-2.56 (m, 1H), 3.51-3.61 (m, 1H), 5.00 (dd, J=11.8, 2.0 Hz, 1H), 5.13 (dd, J=11.3, 3.8 Hz, 1H), 5.47-5.55 (m, 1H), 7.39-7.45 (m, 1H), 7.57-7.66 (m, 2H), 12.62 (br s, 1H). MS (ESI$^+$) m/z 428 (M+H)$^+$.

Example 10

N-[3-(cyclopropylcarbonyl)-4-methyl-4,6-dihydrothieno[2,3-c]furan-2-yl]-2-fluoro-6-(trifluoromethyl)benzamide

Example 10A (2-amino-4-methyl-4,6-dihydro-thieno[2,3-c]furan-3-yl)-cyclopropylmethanone The title compound was prepared according to the procedure outlined in Example 1A substituting 3-cyclopropyl-3- oxopropanenitrile for ethyl cyanoacetate. $^1$H NMR (DMSO-$d_6$, 300 MHz) δ 0.78-0.82 (m, 2H), 0.85-0.93 (m, 1H), 1.00-1.06 (m, 1H), 1.36 (d, J=6.1 Hz, 3H), 1.89-1.97 (m, 1H), 4.75 (dd, J=10.8, 2.0 Hz, 1H), 4.84 (dd, J=10.8, 4.4 Hz, 1H), 5.40-5.49 (m, 1H), 8.18 (br s, 2H). LC-MS (ESI$^+$) m/z 224 (M+H)$^+$.

Example 10B

N-[3-(cyclopropylcarbonyl)-4-methyl-4,6-dihydrothieno[2,3-c]furan-2-yl]-2-fluoro-6-(trifluoromethyl)benzamide The title compound was prepared according to the procedure outlined in Example 1B, substituting Example 10A for Example 1A. $^1$H NMR (DMSO-$d_6$, 300 MHz) δ 0.95-1.06 (m, 2H), 1.08-1.19 (m, 2H), 1.41 (d, J=6.1 Hz, 3H), 2.22-2.30 (m, 1H), 4.95 (dd, J=11.8, 1.7 Hz, 1H), 5.05 (dd, J=11.8, 4.1 Hz, 1H), 5.59-6.67 (m, 1H), 7.74-7.88 (m, 3H), 12.28 (br s, 1H). MS (ESI$^+$) m/z 414 (M+H)$^+$. Anal. calcd. for $C_{19}H_{15}F_4NO_3S$: C, 55.20; H, 3.66; N, 3.39. Found: C, 55.23; H, 3.36; N, 3.39.

Example 11

N-[3-(cyclopentylcarbonyl)-4-methyl-4,6-dihydrothieno[2,3-c]furan-2-yl]-2-fluoro-6-(trifluoromethyl)benzamide

Example 11A (2-amino-4-methyl-4,6-dihydro-thieno[2,3-c]furan-3-yl)-cyclopentylmethanone The title compound was prepared according to the procedure outlined in Example 1A substituting 3-cyclopentyl-3-oxopropanenitrile for ethyl cyanoacetate. LC-MS (ESI$^+$) m/z 252 (M+H)$^+$.

Example 11B

N-[3-(cyclopentylcarbonyl)-4-methyl-4,6-dihydrothieno[2,3-c]furan-2-yl]-2-fluoro-6-(trifluoromethyl)benzamide The title compound was prepared according to the procedure outlined in Example 1B, substituting Example 11A for Example 1A. $^1$H NMR (DMSO-$d_6$, 300 MHz) δ 1.33 (d, J=6.1 Hz, 3H), 1.44-1.74 (m, 6H), 1.84-1.95 (m, 2H), 3.30-3.37 (m, 1H), 4.91 (dd, J=11.8, 2.0 Hz, 1H), 5.01 (dd, J=11.8, 3.8 Hz, 1H), 5.41-5.49 (m, 1H), 7.75-7.88 (m, 3H), 12.13 (br s, 1H). MS (ESI$^+$) m/z 442 (M+H)$^+$. Anal. calcd. for $C_{21}H_{19}F_4NO_3S$: C, 57.14; H, 4.34; N, 3.17. Found: C, 57.15; H, 4.14; N, 3.22.

Example 12

2-chloro-N-[3-(cyclobutylcarbonyl)-4-methyl-4,6-dihydrothieno[2,3-c]furan-2-yl]-6-fluorobenzamide The title compound was prepared according to the procedure outlined in Example 1B, substituting Example 9A for Example 1A and substituting 2-chloro-6-fluorobenzoyl chloride for 2-fluoro-6-trifluoromethylbenzoyl chloride. $^1$H NMR (DMSO-$d_6$, 300 MHz) δ 1.34 (D, J=6.1 Hz, 3H), 1.74-1.86 (m, 1H), 1.91-2.13 (m, 3H), 2.20-2.39 (m, 2H), 3.66-3.76 (m, 1H), 4.90 (dd, J=11.8, 2.0 Hz, 1H), 5.00 (dd, J=12.0, 4.0 Hz, 1H), 5.41-5.47 (m, 1H), 7.46 (t, J=8.8, 8.1 Hz, 1H), 7.52 (d, J=8.1 Hz, 1H), 7.61-7.69 (m, 1H), 12.17 (br s, 1H). MS (ESI$^+$) m/z 394 (M+H)$^+$. Anal. calcd. for $C_{19}H_{17}ClFNO_3S$: C, 57.94; H, 4.35; N, 3.56. Found: C, 57.83; H, 4.27; N, 3.50.

Example 13

N-(3-benzoyl-4-methyl-4,6-dihydrothieno[2,3-c]furan-2-yl)-3-chloro-2-fluoro-6-(trifluoromethyl)benzamide The title compound was prepared according to the procedure outlined in Example 1B, substituting Example 8A for Example 1A and substituting 3-chloro-2-fluoro-6-trifluoromethylbenzoyl chloride for 2-fluoro-6-trifluoromethylbenzoyl chloride. $^1$H NMR (CDCl$_3$, 300 MHz) δ 0.70 (d, J=5.8 Hz, 3H), 5.07 (br s, 3H), 7.43-7.83 (m, 7H), 12.12 (br s, 1H). MS (ESI$^+$) m/z 484 (M+H)$^+$.

Example 14

N-[3-(cyclobutylcarbonyl)-4-methyl-4,6-dihydrothieno[2,3-c]furan-2-yl]-N'-(1-cyclopropyl-1-methylethyl)urea To a 20-mL scintillation vial containing a magnetic stir bar were added Example 9A (83 mg, 0.35 mmol), anhydrous tetrahydrofuran (3 mL), and triethylamine (120 mg, 165 μL, 1.2 mmol). A solution of triphosgene (39 mg, 0.13 mmol) in a few drops of anhydrous tetrahydrofuran was added, and the mixture was stirred at room temperature overnight. A slurry of 1-cyclopropyl-1-methylethylamine p-toluenesulfonic acid salt (326 mg, 1.20 mmol) and triethylamine (120 mg, 165 μL, 1.2 mmol) in anhydrous tetrahydrofuran (2 mL) was added and the mixture was stirred for an additional 24 hours. Saturated sodium bicarbonate solution (10 mL) was added and the mixture was extracted with dichloromethane (3×8 mL). The combined organic extracts were dried over magnesium sulfate, filtered, and concentrated under reduced pressure. The residue was purified by flash chromatography (silica gel: 25% ethyl acetate in hexanes, R$_f$~0.3) to provide the title compound. $^1$H NMR (DMSO-$d_6$, 300 MHz) δ 0.31-0.36 (m, 4H), 1.18 (s, 3H), 1.19 (s, 3H), 1.22-1.28 (m, 1H), 1.31 (d, J=6.1 Hz, 3H), 1.80-2.14 (m, 4H), 2.20-2.44 (m, 2H), 3.46-3.58 (m, 1H), 4.78 (dd, J=11.5, 1.9 Hz, 1H), 4.91 (dd, J=11.2, 4.1 Hz, 1H), 5.37-5.44 (m, 1H), 7.86 (br s, 1H), 11.21 (br s, 1H). MS (ESI$^+$) m/z 363 (M+H)$^+$. Anal. calcd. for $C_{19}H_{26}N_2O_3S$: C, 62.96; H, 7.23; N, 7.73. Found: C, 62.65; H, 7.28; N, 7.49.

Example 15 ethyl 2-[(2,6-difluorobenzoyl)amino]-4-methyl-4,6-dihydrothieno[2,3-c]furan-3-carboxylate The title compound was prepared according to the procedure outlined in Example 1B, substituting 2,6-difluorobenzoyl chloride for 2-fluoro-6-trifluoromethylbenzoyl chloride. $^1$H NMR (CDCl$_3$, 300 MHz) δ 1.30 (t, J=7.0 Hz, 3H), 1.40 (d, J=6.1 Hz, 3H), 4.20-4.38 (m, 2H), 4.89 (dd, J=11.8, 2.0 Hz, 1H), 5.03 (dd, J=11.8, 4.1 Hz, 1H), 5.26-5.34 (m, 1H), 7.28-7.36 (m, 2H), 7.65-7.75 (m, 1H), 11.55 (s, 1H). MS (ESI$^+$) m/z 368 (M+H)$^+$. Anal. calcd. for $C_{17}H_{15}F_2NO_4S$: C, 55.58; H, 4.12; N, 3.81. Found: C, 55.46; H, 3.97; N, 3.69.

Example 16

2-fluoro-N-[3-(2-furoyl)-4-methyl-4,6-dihydrothieno[2,3-c]furan-2-yl]-6-(trifluoromethyl)benzamide

Example 16A (2-amino-4-methyl-4,6-dihydrothieno[2,3-c]furan-3-yl)-furan-2-ylmethanone The title compound was prepared according to the procedure outlined in Example 1A substituting 3-furan-2-yl-3-oxopropionitrile for ethyl cyanoacetate. LC-MS (ESI$^+$) m/z 250 (M+H)$^+$.

Example 16B 2-fluoro-N-[3-(2-furoyl)-4-methyl-4,6-dihydrothieno[2,3-c]furan-2-yl]-6

The title compound was prepared according to the procedure outlined in Example 1B, substituting Example 16A for Example 1A. $^1$H NMR (DMSO-d$_6$, 300 MHz) 051.03 (d, J=6.1 Hz, 3H), 4.94-5.04 (m, 2H), 5.23-5.32 (m, 1H), 6.74 (dd, J=3.4, 1.7 Hz, 1H), 7.29 (d, J=2.7 Hz, 1H), 7.66-7.81 (m, 3H), 8.08 (d, J=1.7 Hz, 1H), 11.87 (br s, 1H). MS (ESI$^+$) m/z 440 (M+H)$^+$. Anal. calcd. for C$_{20}$H$_{13}$F$_4$NO$_4$S: C, 54.67; H, 2.98; N, 3.19. Found: C, 54.61; H, 2.71; N, 3.13.

Example 17 ethyl 2-[(2-chloro-6-fluorobenzoyl)amino]-4-methyl-4,6-dihydrothieno[2,3-c]furan-3-carboxylate The title compound was prepared according to the procedure outlined in Example 1B, substituting 2-chloro-6-fluorobenzoyl chloride for 2-fluoro-6-trifluoromethylbenzoyl chloride. $^1$H NMR (DMSO-d$_6$, 300 MHz) δ 1.28 (t, J=7.1 Hz, 3H), 1.40 (d, J=6.1 Hz, 3H), 4.20-4.32 (m, 2H), 4.90 (dd, J=11.5, 1.7 Hz, 1H), 5.03 (dd, J=11.8, 4.1 Hz, 1H), 5.26-5.34 (m, 1H), 7.40-7.51 (m, 2H), 7.59-7.67 (m, 1H), 11.45 (Br s, 1H). MS (ESI$^+$) m/z 384 (M+H)$^+$. Anal. calcd. for C$_{17}$H$_{15}$F$_2$NO$_4$S: C, 53.20; H, 3.94; N, 3.65. Found: C, 53.30; H, 3.81; N, 3.63.

Example 18 ethyl 2-{[2-fluoro-6-(trifluoromethyl)benzoyl]amino}-4,4,6,6-tetramethyl-4,6-dihydrothieno[2,3-c]furan-3-carboxylate

Example 18A 2-amino-4,4,6,6-tetramethyl-4,6-dihydrothieno[2,3-c]furan-3-carboxylic acid ethyl ester The title compound was prepared according to the procedure outlined in Example 1A substituting 2,2,5,5-tetramethyldihydro-furan-3-one for 2-methyltetrahydro-furan-3-one. $^1$H NMR (DMSO-d$_6$, 300 MHz) δ 1.26 (t, J=7.1 Hz, 3H), 1.36 (s, 6H), 1.47 (s, 6H), 4.19 (q, J=7.1 Hz, 2H), 7.43 (br s, 2H). LC-MS (ESI$^+$) m/z 270 (M+H)$^+$.

Example 18B ethyl 2-{[2-fluoro-6-(trifluoromethyl)benzoyl]amino}-4,4,6,6-tetramethyl-4,6-dihydrothieno[2,3-c]furan-3-carboxylate The title compound was prepared according to the procedure outlined in Example 1B, substituting Example 18A for Example 1A. $^1$H NMR (DMSO-d$_6$, 300 MHz) δ 1.28 (t, J=7.1 Hz, 3H), 1.49 (s, 6H), 1.54 (s, 6H), 4.28 (q, J=7.1 Hz, 2H), 7.74-7.88 (m, 3H), 11.62 (br s, 1H). MS (ESI$^+$) m/z 460 (M+H)$^+$. Anal. calcd. for C$_{21}$H$_{21}$F$_4$NO$_4$S: C, 54.90; H, 4.61; N, 3.05. Found: C, 54.93; H, 4.56; N, 2.89.

Example 19 ethyl 2-{[5-chloro-2-(trifluoromethyl)benzoyl]amino}-4,4,6,6-tetramethyl-4,6-dihydrothieno[2,3-c]furan-3-carboxylate The title compound was prepared according to the procedure outlined in Example 1B, substituting Example 18A for Example 1A and substituting 5-chloro-2-trifluoromethylbenzoyl chloride for 2-fluoro-6-trifluoromethylbenzoyl chloride. $^1$H NMR (DMSO-d$_6$, 300 MHz) δ 1.31 (t, J=7.1 Hz, 3H), 1.49 (s, 6H), 1.54 (s, 6H), 4.30 (q, J=7.1 Hz, 2H), 7.87-8.00 (m, 3H), 11.47 (br s, 1H). MS (ESI$^+$) m/z 476 (M+H)$^+$.

Example 20 ethyl 4,4,6,6-tetramethyl-2-{[(2,2,3,3-tetramethylcyclopropyl)carbonyl]amino}-4,6-dihydrothieno[2,3-c]furan-3-carboxylate The title compound was prepared according to the procedure outlined in Example 1B, substituting Example 18A for Example 1A and substituting 2,2,3,3-tetramethylcyclopropanecarbonyl chloride for 2-fluoro-6-trifluoromethylbenzoyl chloride. NMR (DMSO-d$_6$, 300 MHz) δ 1.21 (s, 6H), 1.23 (s, 6H), 1.33 (t, J=7.1 Hz, 3H), 1.43 (s, 6H), 1.51 (s, 6H), 1.58 (s, 1H), 4.33 (q, J=7.1 Hz, 2H), 11.12 (br s, 1H). MS (ESI$^+$) m/z 394 (M+H)$^+$. Anal. calcd. for C$_{21}$H$_{31}$NO$_4$S: C, 64.09; H, 7.94; N, 3.56. Found: C, 63.74; H, 8.04; N, 3.52.

Example 22 ethyl 2-{[(1-methoxybicyclo[2.2.2]oct-2-yl)carbonyl]amino}-4,4,6,6-tetramethyl-4,6-dihydrothieno[2,3-c]furan-3-carboxylate

Example 22A 1-methoxy-bicyclo[2.2.2]octane-2-carboxylic acid methyl ester

To a 100-mL, round-bottomed flask containing a magnetic stir bar were added 5% palladium/carbon catalyst (100 mg) and methanol (20 mL). Neat 1-methoxybicyclo[2.2.2]oct-5-ene-2-carboxylic acid methyl ester (1.96 g, 1.80 mL, 10.0 mmol) was added. A balloon containing H$_2$ gas was attached and the mixture was stirred at room temperature overnight. The catalyst was removed by vacuum filtration through a small plug of silica gel and the solvent was removed under reduced pressure to provide the title compound. NMR (DMSO-d$_6$, 300 MHz) δ 1.40-1.89 (m, 11H), 2.87 (ddd, J=10.5, 6.4, 2.0 Hz, 1H), 3.07 (s, 3H), 3.57 (s, 3H). MS (ESI$^+$) m/z 200 (M+H)$^+$.

Example 22B 1-methoxy-bicyclo[2.2.2]octane-2-carboxylic acid

The title compound was prepared according to the procedure outlined in Example 2A substituting Example 22A for Example 2A. MS (ESI$^+$) m/z 185 (M+H)$^+$.

Example 22C ethyl 2-{[(1-methoxybicyclo[2.2.2]oct-2-yl)carbonyl]amino}-4,4,6,6-tetramethyl-4,6-dihydrothieno[2,3-c]furan-3-carboxylate The title compound was prepared according to the procedure outlined in Example 1B, substituting Example 18A for Example 1A and substituting the acid chloride of Example 22B (prepared by the treatment of Example 22B with thionyl chloride) for 2-fluoro-6-trifluoromethylbenzoyl chloride. $^1$NMR (DMSO-d$_6$, 300 MHz) δ 1.32 (t, J=7.1 Hz, 3H), 1.45 (s, 6H), 1.52 (s, 6H), 2.27-2.34 (m, 1H), 1.50-1.88 (m, 10H), 2.92 (ddd, J=10.8, 3.5, 2.0 Hz, 1H), 3.20 (s, 3H), 4.32 (q, J=7.1 Hz, 2H), 11.63 (br s, 1H). MS (ESI$^+$) m/z 436 (M+H)$^+$. Anal. calcd. for C$_{23}$H$_{33}$NO$_5$S: C, 63.42; H, 7.64; N, 3.22. Found: C, 64.01; H, 6.91; N, 3.06.

Example 23 ethyl 4,4,6,6-tetramethyl-2-({[(1S,2R,4R)-2-methylbicyclo[2.2.1]hept-2-yl]carbonyl}amino)-4,6-dihydrothieno[2,3-c]furan-3-carboxylate The title compound was prepared according to the procedure outlined in Example 1B, substituting Example 18A for Example 1A and substituting the acid chloride of 2-methylbicyclo[2.2.1]heptane-2-carboxylic acid (prepared by the treatment of and 2-methylbicyclo[2.2.1]heptane-2-carboxylic acid with thionyl chloride) for 2-fluoro-6-trifluoromethylbenzoyl chloride. $^1$NMR (DMSO-d$_6$, 300 MHz) δ 1.26-1.28 (m, 2H), 1.30 (s, 3H), 1.33 (t, J=7.1 Hz, 3H), 1.45 (s, 6H), 1.47-1.50 (m, 2H), 1.52 (s, 6H), 1.57-1.72 (m, 2H), 2.21-2.25 (m, 2H), 2.39-2.42 (m, 2H), 4.35 (q, J=7.1 Hz, 2H), 11.38 (br s, 1H); MS (ESI$^+$) m/z 406 (M+H)$^+$.

Example 24

4,4,6,6-tetramethyl-N-propyl-2-{[(2,2,3,3-tetramethylcyclopropyl)carbonyl]amino}-4,6-dihydrothieno[2,3-c]furan-3-carboxamide Example 24A 4,4,6,6-Tetramethyl-2-[(2,2,3,3-tetramethyl-cyclopropanecarbonyl)-amino]-4,6-dihydrothieno[2,3-c]furan-3-carboxylic acid The title compound was prepared following the procedure outlined in Example 2A substituting Example 20 for Example 2A. LC-MS (ESI$^+$) m/z 366 (M+H)$^+$.

Example 24B 4,4,6,6-tetramethyl-N-propyl-2-{[(2,2,3,3-tetramethylcyclopropyl)carbonyl]amino}-4,6-dihydrothieno[2,3-c]furan-3-carboxamide The title compound was prepared following the procedure outlined in Example 2B substituting Example 24A for Example 2A and substituting propylamine for 3,3-difluoroazetidine. $^1$H NMR (DMSO-d$_6$, 300 MHz) δ 0.88 (t, J=7.5 Hz, 3H), 1.16 (s, 6H), 1.22 (s, 6H), 1.42 (s, 6H), 1.43 (s, 6H), 1.48-1.53 (m, 3H), 3.17 (q, J=6.8 Hz, 2H), 7.90 (br s, 1H), 10.48 (br s, 1H); MS (ESI$^+$) m/z 407 (M+H)$^+$.

Example 26 ethyl 4-methyl-2-{[(2,2,3,3-tetramethylcyclopropyl)carbonyl]amino}-4,6-dihydrothieno[2,3-c]furan-3-carboxylate The title compound was prepared according to the procedure outlined in Example 1B, substituting 2,2,3,3-tetramethyl-cyclopropanecarbonyl chloride for 2-fluoro-6-trifluoromethylbenzoyl chloride. $^1$H NMR (DMSO-d$_6$, 300 MHz) δ 1.21 (s, 6H), 1.23 (s, 6H), 1.31 (t, J=7.0 Hz, 3H), 1.37 (d, J=6.4 Hz, 3H), 1.59 (s, 1H), 4.20-4.38 (m, 2H), 4.83 (dd, J=11.5, 1.7 Hz, 1H), 4.96 (dd, J=11.5, 4.4 Hz, 1H), 5.22-5.30 (m, 1H), 10.91 (br s, 1H). MS (ESI$^+$) m/z 352 (M+H)$^+$. Anal. calcd. for C$_{18}$H$_{25}$NO$_4$S: C, 61.51; H, 7.17; N, 3.99. Found: C, 61.23; H, 7.26; N, 4.17.

Example 27 ethyl 4-methyl-2-({[(1S,2R,4R)-2-methylbicyclo[2.2.1]hept-2-yl]carbonyl}amino)-4,6-dihydrothieno[2,3-c]furan-3-carboxylate The title compound was prepared according to the procedure outlined in Example 1B, substituting the acid chloride of 2-methylbicyclo[2.2.1]heptane-2-carboxylic acid (prepared by the treatment of and 2-methylbicyclo[2.2.1]heptane-2-carboxylic acid with thionyl chloride) for 2-fluoro-6-trifluoromethylbenzoyl chloride. $^1$H NMR (DMSO-d$_6$, 300 MHz) δ 0.96 (dd, J=12.4, 2.2 Hz, 1H), 1.07-1.26 (m, 3H), 1.30 (s, 3H), 1.31 (t, J=7.0 Hz, 3H), 1.38 (d, J=6.1 Hz, 3H), 1.44-1.54 (m, 2H), 1.65-1.73 (m, 1H), 2.22-2.25 (m, 1H), 2.34-2.42 (m, 2H), 4.22-4.41 (m, 2H), 4.84 (dd, J=11.8, 2.0 Hz, 1H), 4.98 (dd, J=11.5, 3.7 Hz, 1H), 5.22-5.30 (m, 1H), 11.14 (br s, 1H). MS (ESI$^+$) m/z 352 (M+H)$^+$. Anal. calcd. for C$_{14}$H$_{25}$NO$_4$S: C, 62.78; H, 6.93; N, 3.85. Found: C, 62.83; H, 6.94; N, 3.81.

Example 28

N-{3-[(3,3-difluoroazetidin-1-yl)carbonyl]-4-methyl-4,6-dihydrothieno[2,3-c]furan-2-yl}-2,2,3,3-tetramethylcyclopropanecarboxamide Example 28A 4-methyl-2-[(2,2,3,3-tetramethylcyclopropanecarbonyl)-amino]-4,6-dihydro-thieno[2,3-c]furan-3-carboxylic acid The title compound was prepared according to the procedure outlined in Example 2A substituting Example 26 for Example 1B. LC-MS (ESI$^+$) m/z 324 (M+H)$^+$.

Example 28B

N-{3-[(3,3-difluoroazetidin-1-yl)carbonyl]-4-methyl-4,6-dihydrothieno[2,3-c]furan-2-yl}-2,2,3,3-tetramethylcyclopropanecarboxamide The title compound was prepared according to the procedure outlined in Example 2B substituting Example 28A for Example 2A. $^1$H NMR (CDCl$_3$, 300 MHz) δ 1.13 (s, 1H), 1.24 (br s, 6H), 1.33 (br s, 6H), 1.39 (d, J=6.1 Hz, 3H), 4.24-4.36 (m, 2H), 4.58-4.70 (m, 2H), 4.97-5.06 (m, 2H), 5.27-5.37 (m, 1H), 10.89 (br s, 1H). MS (ESI$^+$) m/z 399 (M+H)$^+$.

Example 29

5-chloro-N-{3-[(3,3-difluoroazetidin-1-yl)carbonyl]-4-methyl-4,6-dihydrothieno[2,3-c]furan-2-yl}-2-methoxybenzamide

Example 29A 2-(5-chloro-2-methoxybenzoylamino)-4-methyl-4,6-dihydrothieno[2,3-c]furan-3-carboxylic acid ethyl ester The title compound was prepared according to the procedure outlined in Example 1B, substituting 5-chloro-2-methoxybenzoyl chloride for 2-fluoro-6-trifluoromethylbenzoyl chloride. $^1$H NMR (DMSO-d$_6$, 300 MHz) δ 1.33 (t, J=7.1 Hz, 3H), 1.41 (d, J=6.1 Hz, 3H), 4.14 (s, 3H), 4.26-4.45 (m, 2H), 4.89 (dd, J=11.5, 1.7 Hz, 1H), 5.22 (dd, J=11.9, 4.1 Hz, 1H), 5.27-5.34 (m, 1H), 7.36 (d, J=8.8 Hz, 1H), 7.72 (dd, J=9.0, 2.9 Hz, 1H), 8.04 (d, J=3.0 Hz, 1H), 12.88 (br s, 1H). MS (ESI$^+$) m/z 396 (M+H)$^+$.

Example 29B 2-(5-chloro-2-methoxybenzoylamino)-4-methyl-4,6-dihydrothieno[2,3-c]furan-3-carboxylic acid The title compound was prepared according to the procedure outlined in Example 2A substituting Example 29A for Example 1B. LC-MS (ESI$^+$) m/z 368 (M+H)$^+$.

Example 29C 5-chloro-N-{3-[(3,3-difluoroazetidin-1-yl)carbonyl]-4-methyl-4,6-dihydrothieno[2,3-c]furan-2-yl}-2-methoxybenzamide The title compound was prepared according to the procedure outlined in Example 2B substituting Example 29B for Example 2A. $^1$H NMR (CDCl$_3$, 300 MHz) δ 1.31 (d, J=6.1 Hz, 3H), 4.11 (s, 3H), 4.41-4.53 (m, 2H), 4.59-4.71 (m, 2H), 4.90-5.02 (m, 2H), 5.34-5.42 (m, 1H), 7.34 (d, J=9.1 Hz, 1H), 7.69 (dd, J=9.0, 2.9 Hz, 1H), 8.00 (d, J=2.7 Hz, 1H), 12.43 (br s, 1H). MS (ESI$^+$) m/z 443 (M+H)$^+$. Anal. calcd. for C$_{19}$H$_{17}$ClF$_2$N$_2$O$_4$S: C, 51.53; H, 3.87; N, 6.33. Found: C, 51.54; H, 3.59; N, 6.25.

Example 30

2-fluoro-N-{3-[(3-hydroxyazetidin-1-yl)carbonyl]-4-methyl-4,6-dihydrothieno[2,3-c]furan-2-yl}-6-(trifluoromethyl)benzamide The title compound was prepared according to the procedure outlined in Example 2B substituting 3-hydroxyazetidine hydrochloride for 3,3-difluoroazetidine hydrochloride. $^1$H NMR (DMSO-d$_6$, 300 MHz) δ 1.29 (d, J=6.1 Hz, 3H), 3.62-3.67 (m, 1H), 3.74-3.79 (m, 1H), 4.03-4.08 (m, 1H), 4.15-4.24 (m, 1H), 4.40-4.48 (m, 1H), 4.88-5.01 (m, 2H), 5.14-5.20 (m, 1H), 5.74 (d, J=5.8 Hz, 1H), 7.67-7.81 (m, 3H), 11.71 (br s, 1H). MS (ESI$^+$) m/z 445 (M+H)$^+$.

Example 31

N-(3-benzoyl-4-methyl-4,6-dihydrothieno[2,3-c]furan-2-yl)-2,2,3,3-tetramethylcyclopropanecarboxamide The title compound was prepared according to the procedure outlined in Example 1B, substituting Example 8A for Example 1A and substituting 2,2,3,3-tetramethylcyclopropanecarbonyl chloride for 2-fluoro-6-trifluoromethylbenzoyl chloride. $^1$H NMR (CDCl$_3$, 300 MHz) δ 0.63 (d, J=5.8 Hz, 3H), 1.17 (s, 3H), 1.21 (s, 3H), 1.22 (s, 3H), 1.24 (s, 3H), 1.55 (br s, 1H), 4.90 (br s, 3H), 7.52-7.57 (m, 2H), 7.61-7.67 (m, 3H), 11.46 (br s, 1H). MS (ESI$^+$) m/z 384 (M+H)$^+$.

Example 32

N-[3-(cyclobutylcarbonyl)-4-methyl-4,6-dihydrothieno[2,3-c]furan-2-yl]-2,2,3,3-tetramethylcyclopropanecarboxamide The title compound was prepared according to the procedure outlined in Example 1B, substituting Example 9A for Example 1A and substituting 2,2,3,3-tetramethylcyclopropanecarbonyl chloride for 2-fluoro-6-trifluoromethylbenzoyl chloride. $^1$H NMR (DMSO-d$_6$, 300 MHz) δ 1.22-1.24 (m, 12H), 1.33 (d, J=6.1 Hz, 3H), 1.58 (s, 1H), 1.81-1.91 (m, 1H), 1.94-2.14 (m, 3H), 2.21-2.30 (m, 1H), 2.33-2.45 (m, 1H), 4.83 (dd, J=11.5, 1.0 Hz, 1H), 4.95 (dd, J=11.5, 4.1 Hz, 1H), 5.41-5.48 (m, 1H), 12.07 (br s, 1H). MS (ESI$^+$) m/z 362 (M+H)$^+$. Anal. calcd. for C$_{20}$H$_{27}$NO$_3$S: C, 66.45; H, 7.53; N, 3.87. Found: C, 66.01; H, 7.50; N, 3.75.

Example 33

N-[3-(cyclobutylcarbonyl)-4-methyl-4,6-dihydrothieno[2,3-c]furan-2-yl]hexahydro-2,5-methanopentalene-3a(1H)-carboxamide The title compound was prepared according to the procedure outlined in Example 1B, substituting Example 9A for Example 1A and substituting hexahydro-2,5-methanopentalene-3a-carbonyl chloride for 2-fluoro-6-trifluoromethylbenzoyl chloride. $^1$H NMR (DMSO-d$_6$, 300 MHz) δ 1.35 (d, J=6.1 Hz, 3H), 1.63-1.70 (m, 4H), 1.79-2.13 (m, 10H), 2.31-2.31 (m, 2H), 2.37 (br s, 2H), 2.64-2.69 (m, 1H), 3.54-3.65 (m, 1H), 4.85 (dd, J=11.5, 1.9 Hz, 1H), 4.96 (dd, J=11.5, 3.7 Hz, 1H), 5.43-5.51 (m, 1H), 12.42 (br s, 1H). MS (ESI$^+$) m/z 362 (M+H)$^+$. Anal. calcd. for C$_{22}$H$_{27}$NO$_3$S: C, 68.54; H, 7.06; N, 3.63. Found: C, 68.35; H, 6.84; N, 3.55.

Example 34

N-[3-(cyclopropylcarbonyl)-4-methyl-4,6-dihydrothieno[2,3-c]furan-2-yl]hexahydro-2,5-methanopentalene-3a(1H)-carboxamide The title compound was prepared according to the procedure outlined in Example 1B, substituting Example 10A for Example 1A and substituting hexahydro-2,5-methanopentalene-3a-carbonyl chloride for 2-fluoro-6-trifluoromethylbenzoyl chloride. ¹H NMR (DMSO-d₆, 300 MHz) δ 0.99-1.06 (m, 2H), 1.08-1.15 (m, 1H), 1.20-1.26 (m, 1H), 1.41 (d, J=6.1 Hz, 3H), 1.76-1.83 (m, 4H), 1.85-1.90 (m, 2H), 1.98-2.02 (m, 2H), 2.15-2.23 (m, 1H), 2.34 (br s, 2H), 2.61-2.65 (m, 1H), 4.91 (J=11.5, 1.7 Hz, 1H), 4.99 (11.5, 4.1 Hz, 1H), 5.60-5.68 (m, 1H), 12.33 (br s, 1H). MS (ESI⁺) m/z 372 (M+H)⁺. Anal. calcd. for C₂₁H₂₅NO₃S: C, 67.89; H, 6.78; N, 3.77. Found: C, 67.85; H, 6.87; N, 3.77.

Example 35

N-[3-(cyclopentylcarbonyl)-4-methyl-4,6-dihydrothieno[2,3-c]furan-2-yl]hexahydro-2,5-methanopentalene-3a(1H)-carboxamide The title compound was prepared according to the procedure outlined in Example 1B, substituting Example 11A for Example 1A and substituting hexahydro-2,5-methanopentalene-3a-carbonyl chloride for 2-fluoro-6-trifluoromethylbenzoyl chloride. ¹H NMR (DMSO-d₆, 300 MHz) δ 1.36 (d, J=6.1 Hz, 3H), 1.50-1.84 (m, 12H), 1.88-2.05 (m, 6H), 2.35 (br s, 2H), 2.63-2.67 (m, 1H), 3.12-3.22 (m, 1H), 4.87 (dd, J=11.5, 1.0 Hz, 1H), 4.98 (dd, J=11.5, 3.7 Hz, 1H), 5.46-5.54 (m, 1H), 12.39 (br s, 1H). LC-MS (ESI⁺) m/z 400 (M+H)⁺. Anal. calcd. for C₂₃H₂₉NO₃S: C, 69.14; H, 7.32; N, 3.51. Found: C, 69.02; H, 7.45; N, 3.49.

Example 36

N-[3-(2-furoyl)-4-methyl-4,6-dihydrothieno[2,3-c]furan-2-yl]hexahydro-2,5-methanopentalene-3a(1H)-carboxamide The title compound was prepared according to the procedure outlined in Example 1B, substituting Example 16A for Example 1A and substituting hexahydro-2,5-methanopentalene-3a-carbonyl chloride for 2-fluoro-6-trifluoromethylbenzoyl chloride. ¹H NMR (DMSO-d₆, 300 MHz) δ 0.87 (d, J=6.1 Hz, 3H), 1.56-1.68 (m, 4H), 1.77-1.91 (m, 4H), 2.00-2.04 (m, 2H), 2.34 (br s, 2H), 2.64-2.66 (m, 1H), 4.96 (d, J=3.4 Hz, 2H), 5.48-5.56 (m, 1H), 6.80 (dd, J=3.4, 1.7 Hz, 1H), 7.41-7.42 (m, 1H), 8.08-8.09 (m, 1H), 11.72 (br s, 1H). LC-MS (ESI⁺) m/z 398 (M+H)⁺. Anal. calcd. for C₂₂H₂₃NO₄S: C, 66.48; H, 5.83; N, 3.52. Found: C, 66.43; H, 5.54; N, 3.57.

Example 37

N-[3-(cyclobutylcarbonyl)-4-methyl-4,6-dihydrothieno[2,3-c]furan-2-yl]-2,2-dimethyl-4-oxo-3,4-dihydro-2H-pyran-6-carboxamide To a solution of 6,6-dimethyl-4-oxo-5,6-dihydro-4H-pyran-2-carboxylic acid (0.35 g, 2.0 mmol, commercially available from Aldrich) in 8 mL of methylene chloride at 0° C. was added oxalyl chloride (0.19 mL, 2.3 mmol) dropwise and 2 drops of dimethylformamide. The mixture was stirred at 0° C. for 10 minutes and then warmed to ambient temperature and allowed to stir for an additional 1 hour. The mixture was concentrated under reduced pressure to provide 6,6-dimethyl-4-oxo-5,6-dihydro-4H-pyran-2-carbonyl chloride The product of Example 9A (60 mg, 0.30 mmol) was diluted with THF (1 mL) and to it was added the freshly prepared 6,6-dimethyl-4-oxo-5,6-dihydro-4H-pyran-2-carbonyl chloride (55 mg, 0.30 mmol) and triethylamine (0.1 mL, 0.73 mmol). The mixture was heated to 65° C. for 15 hours. The mixture was cooled to ambient temperature then concentrated under reduced pressure. The residue was purified by column chromatography (SiO₂, 20-50% ethyl acetate/hexanes gradient) to provide the title compound. ¹H NMR (CDCl₃, 300 MHz) δ 1.47 (d, J=6.10 Hz, 3H), 1.64 (d, J=5.43 Hz, 6H), 1.92-2.34 (m, 4H) 3.53-3.60 (m, 1H), 4.98 (dd, J=11.53, 1.36 Hz, 1H), 5.11 (dd, J=11.53, 3.73 Hz, 1H), 5.45-5.55 (m, 1H), 6.39 (s, 1H); MS (DCI/NH₃) m/z 290 (M+H)⁺. Anal. Calculated for C₂₀H₂₃NO₅S.0.2H₂O: C, 61.11; H, 6.00; N, 3.56. Found: C, 60.93; H, 5.91; N, 3.43.

Example 38

N-[3-(cyclobutylcarbonyl)-4-methyl-4,6-dihydrothieno[2,3-c]furan-2-yl]-2-ethoxybenzamide The title compound was prepared according to the procedure outlined in Example 1B, substituting Example 9A for Example 1A and substituting 2-ethoxy-benzoyl chloride for 2-fluoro-6-trifluoromethylbenzoyl chloride. ¹H NMR (CDCl₃, 300 MHz) δ 1.47 (d, J=6.10 Hz, 3H), 1.63 (t, J=6.95 Hz, 3H), 1.91-2.35 (m, 5H), 3.47-3.65 (m, 1H), 4.54 (q, J=7.12 Hz, 2H), 5.00 (dd, J=11.19, 1.36 Hz, 2H), 5.12 (dd, J=11.19, 4.07 Hz, 2H), 5.48-5.56 (m, J=8.81 Hz, 1H), 7.03-7.15 (m, 2H), 7.51 (td, J=7.80, 2.03 Hz, 1H), 8.21 (dd, J=8.14, 1.70 Hz, 1H); MS (DCI/NH₃) m/z 386 (M+H)⁺. Anal. Calculated for C₂₁H₂₃NO₄S: C, 65.43; H, 6.01; N, 3.63. Found: C, 64.93; H, 6.18; N, 3.56.

Example 39

2-chloro-N-[3-(cyclobutylcarbonyl)-4-methyl-4,6-dihydrothieno[2,3-c]furan-2-yl]-5-fluorobenzamide The title compound was prepared according to the procedure outlined in Example 1B, substituting Example 9A for Example 1A and substituting 2-chloro-5-fluoro-benzoylchloride for 2-fluoro-6-trifluoromethylbenzoyl chloride. ¹H NMR (CDCl₃, 300 MHz) δ 1.48 (d, J=6.10 Hz, 3H), 1.92-2.35 (m, 5H), 2.49-2.62 (m, 1H), 3.52-3.62 (m, 1H), 5.00 (dd, J=11.53, 1.36 Hz, 2H), 5.13 (dd, J=11.19, 3.73 Hz, 2H), 7.19 (ddd, J=8.82, 7.46, 3.05 Hz, 1H), 7.44-7.56 (m, 2H); MS (DCI/NH₃) m/z 394 (M+H)⁺. Anal. Calculated for C₁₉H₁₇ClFNO₃S: C, 57.94; H, 4.35; N, 3.56. Found: C, 57.57; H, 4.13; N, 3.43.

Example 40

N-[3-(cyclobutylcarbonyl)-4-methyl-4,6-dihydrothieno[2,3-c]furan-2-yl]-2-(trifluoromethoxy)benzamide The title compound was prepared according to the procedure outlined in Example 1B, substituting Example 9A for Example 1A and substituting 2-trifluoromethoxybenzoylchloride for 2-fluoro-6-trifluoromethylbenzoyl chloride. ¹H NMR (CDCl₃, 300 MHz) δ 1.50 (t, J=6.10 Hz, 3H), 1.91-2.37 (m, 5H), 2.50-2.66 (m, 1H), 3.50-3.63 (m, 1H), 5.00 (dd, J=11.53, 1.36 Hz, 1H), 5.13 (dd, J=11.19, 4.07 Hz, 1H), 5.47-5.56 (m, 1H), 7.39-7.45 (m, 1H), 7.48 (dd, J=7.80, 1.02 Hz, 1H), 7.61 (td, J=7.80, 1.70 Hz, 1H), 8.07 (dd, J=7.63, 1.87 Hz, 1H); MS (LCMS) m/z 426 (M+H)⁺.

Example 41 ethyl 2-[(2,6-dichlorobenzoyl)amino]-4-methyl-4,6-dihydrothieno[2,3-c]furan-3-carboxylate The title compound was prepared according to the procedure outlined in Example 1B, substituting 2,6-dichlorobenzoyl chloride for 2-fluoro-6-trifluoromethylbenzoyl chloride. $^1$H NMR (DMSO-d$_6$, 300 MHz) δ 1.27 (t, J=7.1 Hz, 3H), 1.40 (d, J=6.1 Hz, 3H), 4.19-4.32 (m, 2H), 4.90 (dd, J=11.5, 2.0 Hz, 1H), 5.03 (dd, J=11.5, 4.1 Hz, 1H), 6.25-6.34 (m, 1H), 7.54-7.64 (m, 1H), 11.38 (br s, 1H). LC-MS (ESI$^+$) m/z 400 (M+H)$^+$.

Example 42 ethyl 4-methyl-2-{[2-oxatricyclo[3.3.1.1$^{3,7}$]dec-1-ylcarbonyl]amino}-4,6-dihydrothieno[2,3-c]furan-3-carboxylate

Example 42A

2-Oxatricyclo[3.3.1.1$^{3,7}$]decane-1-carboxylic acid

To a solution of 2-oxatricyclo[3.3.1.1$^{3,7}$]decane-1-carboxylic acid methyl ester (2.5 g, 12.6 mmol, prepared as described by Partch, R.; Brewster, W.; Stokes, B., *Croatia Chemical Acta* (1969), 58(4), 661-669) in 1:1 methanol/water (100 mL) was added 5 N aqueous NaOH (3.8 mL, 19 mmol). The mixture was stirred at room temperature for 3 hours and then extracted with methylene chloride to remove unreacted starting material. The aqueous layer was acidified (pH~2) with 6 N aqueous HCl and then extracted with methylene chloride. The combined acidic extracts were dried (Na$_2$SO$_4$), filtered and concentrated to afford 1.92 g of the title compound. MS (ESI$^+$) m/z 183 (M+H)$^+$.

Example 42B ethyl 4-methyl-2-{[2-oxatricyclo[3.3.1.1$^{3,7}$]dec-1-ylcarbonyl]amino}-4,6-dihydrothieno[2,3-c]furan-3-carboxylate To the product of example 42A (0.18 g, 1.0 mmol) was added oxalyl chloride (1.5 mL of 2 M solution in dichloromethane) and N,N-dimethylformamide (20 μL, 0.26 mmol) and the mixture stirred at room temperature for 1 hour. The solvent was removed under reduced pressure, 5 mL of dichloromethane was added and the solvent evaporated to afford the acid chloride. To a solution of the product of Example 1A (0.12 g, 0.5 mmol) in dichloromethane (0.5 mL) was added to the freshly prepared acid chloride and N,N-diisopropylethylamine (0.18 mL, 1.0 mmol). The mixture was stirred at room temperature for 1 hour then diluted with dichloromethane (10 mL) and washed with water and brine. The organic extract was dried over MgSO$_4$ and concentrated under reduced pressure. Purification by chromatography (0 to 35% ethyl acetate in hexanes gradient) afforded the title compound. $^1$H NMR (300 MHz, DMSO-d$_6$) δ ppm 1.31 (t, J=7.12 Hz, 3H) 1.38 (d, J=6.1 Hz, 3H) 1.56-2.08 (m, 11H) 2.19 (s, 2H) 4.19-4.42 (m, 2H) 4.80-4.89 (m, 1H) 4.93-5.02 (m, 1H) 5.19-5.34 (m, 1H) 11.46 (s, 1H). MS (DCI/NH$_3$) m/z 392.1 (M+H)$^+$. Anal. Calculated for C$_{20}$H$_{25}$NO$_5$S.0.2H$_2$O: C, 60.71; H, 6.49; N, 3.54. Found: C, 60.71; H, 6.43; N, 3.50.

Example 43

N-{3-[(3,3-difluoroazetidin-1-yl)carbonyl]-4-methyl-4,6-dihydrothieno[2,3-c]furan-2-yl}-2-oxatricyclo[3.3.1.1$^{3,7}$]decane-1-carboxamide

Example 43A 4-methyl-2-{[2-oxatricyclo[3.3.1.1$^{3,7}$]dec-1-ylcarbonyl]amino}-4,6-dihydrothieno[2,3-c]furan-3-carboxylic acid To a solution of the product from Example 42B in ethanol (3 mL) was added 2 N lithium hydroxide (2 mL) and the mixture was heated at 60° C. for 20 hours. The mixture was cooled to ambient temperature and acidified to pH 1 by the addition of 1 N aqueous HCl. The mixture was extracted twice with ethyl acetate and the combined organic extracts were dried over MgSO$_4$ and concentrated under reduced pressure to afford the title compound. LC/MS (APCI) m/z 364.3 (M+H)$^+$.

Example 43B

N-{3-[(3,3-difluoroazetidin-1-yl)carbonyl]-4-methyl-4,6-dihydrothieno[2,3-c]furan-2-yl}-2-oxatricyclo[3.3.1.1$^{3,7}$]decane-1-carboxamide To a solution of the product from example 43A (90 mg, 0.25 mmol) in N,N-dimethylformamide (0.5 mL) was added O-(benzotriazol-1-yl)-N,N,N',N'-tetramethyluronium hexafluorophosphate (380 mg, 1 mmol), N,N diisopropylethylamine (0.3 mL, 1.7 mmol), and 3,3-difluoroazetidine hydrochloride (130 mg, 1 mmol). The mixture was stirred at room temperature for 18 hours, diluted with ethyl acetate (10 mL) and washed with water and brine. The organic extract was dried over MgSO$_4$ and concentrated. Purification by chromatography (0 to 75% ethyl acetate in hexane gradient) afforded the title compound. $^1$H NMR (300 MHz, DMSO-d$_6$) δ ppm 1.28 (d, J=6.4 Hz, 3H) 1.63-2.06 (m, 11H) 2.18 (s, 2H) 4.35-4.71 (m, 4H) 4.81-5.00 (m, 2H) 5.29-5.42 (m, 1H) 11.12 (s, 1H). MS (DCI/NH$_3$) m/z 439.1 (M+H)$^+$.

Example 44

N-{3-[(3,3-difluoroazetidin-1-yl)carbonyl]-4-methyl-4,6-dihydrothieno[2,3-c]furan-2-yl}hexahydro-2,5-methanopentalene-3a(1H)-carboxamide

Example 44A ethyl 2-[hexahydro-2,5-methanopentalen-3a(1H)-ylcarbonyl)amino]-4-methyl-4,6-dihydrothieno[2,3-c]furan-3-carboxylate The title compound was prepared according to the procedure described in Example 42B substituting 3-noradamantane carboxylic acid for the product of Example 42A. $^1$H NMR (300 MHz, DMSO-d$_6$) δ ppm 1.31 (t, J=7.1 Hz, 3H) 1.38 (d, J=6.1 Hz, 3H) 1.56-1.73 (m, 4H) 1.76-1.86 (m, 2H) 1.86-1.94 (m, 2H) 1.98-2.07 (m, 2H) 2.34 (s, 2H) 2.66 (t, J=6.8 Hz, 1H) 4.17-4.44 (m, 2H) 4.80-4.89 (m, 1H) 4.94-5.02 (m, 1H) 5.19-5.33 (m, 1H) 11.11 (s, 1H). MS (DCI/NH$_3$) m/z 376.1 (M+H)$^+$.

Example 44B 4-methyl-4,6-dihydrothieno[2,3-c]furan-2-yl}hexahydro-2,5-methanopentalene-3a(1H)-carboxylic acid The title compound was prepared according to the procedure described in Example 43A substituting the product of Example 44A for the product of Example 42B. LC/MS (APCI) m/z 348.3 (M+H)$^+$.

Example 44C

N-{3-[(3,3-difluoroazetidin-1-yl)carbonyl]-4-methyl-4,6-dihydrothieno[2,3-c]furan-2-yl}hexahydro-2,5-methanopentalene-3a(1H)-carboxamide The title compound was prepared by the procedure described in Example 43B substituting the product of Example 44B for the product of Example 43A. ¹H NMR (300 MHz, CDCl₃) δ ppm 1.40 (d, J=6.4 Hz, 3H) 1.64-1.76 (m, 4H) 1.84-1.99 (m, 4H) 2.09-2.19 (m, 2H) 2.40 (s, 2H) 2.78 (t, J=6.6 Hz, 1H) 4.31 (q, J=11.5 Hz, 2H) 4.53-4.76 (m, 2H) 4.97-5.11 (m, 2H) 5.25-5.40 (m, 1H) 11.31 (s, 1H). MS (DCI/NH₃) m/z 423.1 (M+H)⁺. Anal. calculated for $C_{21}H_{24}F_2N_2O_3S$: C, 59.70; H, 5.73; N, 6.63. Found: C, 59.77; H, 5.85; N, 6.29.

Example 45

2-{[2-fluoro-6-(trifluoromethyl)benzoyl]amino}-4,4,6,6-tetramethyl-N-propyl-4,6-dihydrothieno[2,3-c]furan-3-carboxamide

Example 45A

2-{[2-fluoro-6-(trifluoromethyl)benzoyl]amino}-4,4,6,6-tetramethyl-4,6-dihydrothieno[2,3-c]furan-3-carboxylic acid The title compound was prepared from the product of Example 18B using the procedure described for Example 2A. LC/MS (ESI⁺) m/z 432 (M+H)⁺.

Example 45B

2-{[2-fluoro-6-(trifluoromethyl)benzoyl]amino}-4,4,6,6-tetramethyl-N-propyl-4,6-dihydrothieno[2,3-c]furan-3-carboxamide The title compound was prepared from the product of Example 45A and propylamine using the procedure described in Example 2B. ¹H NMR (DMSO-d₆, 300 MHz) δ 0.85 (t, J=7.3 Hz, 3H), 1.42-1.49 (m, 2H), 1.44 (s, 6H), 1.48 (s, 6H), 3.08-3.14 (m, 2H), 7.67-7.8 (m, 3H), 8.05 (t, J=5.4 Hz, 1H), 11.54 (br s, 1H). MS (ESI⁺) m/z 473 (M+H)⁺. Anal. calcd. for $C_{22}H_{24}F_4N_2O_3S$: C, 55.92; H, 5.12; N, 5.93. Found: C, 55.39; H, 4.65; N, 5.69.

Example 46

2-{[2-fluoro-6-(trifluoromethyl)benzoyl]amino}-N-(2-methoxyethyl)-4,4,6,6-tetramethyl-4,6-dihydrothieno[2,3-c]furan-3-carboxamide The title compound was prepared from the product of Example 45A and 2-methoxyethylamine using the procedure described for Example 2B. ¹H NMR (DMSO-d₆, 300 MHz) δ 1.45 (s, 6H), 1.48 (s, 6H), 3.18 (s, 3H), 3.31-3.41 (m, 4H), 7.68-7.82 (m, 3H), 7.99 (t, J=5.3 Hz, 1H), 11.51 (br s, 1H). MS (ESI⁺) m/z 489 (M+H)⁺. Anal. calcd. for $C_{22}H_{24}F_4N_2O_4S$: C, 54.09; H, 4.95; N, 5.73. Found: C, 53.88; H, 4.65; N, 5.71.

Example 47 ethyl 4-methyl-2-({[(1S,4R)-4,7,7-trimethyl-3-oxo-2-oxabicyclo[2.2.1]hept-1-yl]carbonyl}amino)-4,6-dihydrothieno[2,3-c]furan-3-carboxylate (1-S)-(−)-Camphanic chloride (0.33 g, 1.5 mmol) was added to a mixture of the compound from Example 1A (0.3 g, 1.3 mmol) and N,N-diisopropylethylamine (0.3 mL, 1.8 mmol) in dichloromethane (1 mL). The reaction mixture was stirred at room temperature for 18 hours then diluted with dichloromethane (10 mL) and washed with water and brine. The organic extract was dried with MgSO₄ and concentrated under reduced pressure. Purification by chromatography (0% to 25% ethyl acetate in hexane gradient) afforded the title compound. ¹H NMR (300 MHz, CDCl₃) δ ppm 0.98 (d, J=4.4 Hz, 3H), 1.16 (d, J=2.0 Hz, 6H) 1.40 (t, J=7.3 Hz, 3H) 1.49 (d, J=6.1 Hz, 3H) 1.69-1.85 (m, 1H) 1.93-2.11 (m, 2H) 2.53-2.66 (m, 1H) 4.26-4.49 (m, 2H) 4.92-5.01 (m, 1H) 5.06-5.17 (m, 1H) 5.34-5.46 (m, 1H) 11.64 (s, 1H). MS (DCI/NH₃) m/z 408.1 (M+H)⁺. Anal. Calculated for $C_{20}H_{25}NO_6S$ (0.3H₂O): C, 58.95; H, 6.18; N, 3.44. Found: C, 58.26; H, 6.20; N, 3.35.

Example 48

(1S,4R)—N-{3-[(3,3-difluoroazetidin-1-yl)carbonyl]-4-methyl-4,6-dihydrothieno[2,3-c]furan-2-yl}-4,7,7-trimethyl-3-oxo-2-oxabicyclo[2.2.1]heptane-1-carboxamide

Example 48A 4-methyl-2-({[(1S,4R)-4,7,7-trimethyl-3-oxo-2-oxabicyclo[2.2.1]hept-1-yl]carbonyl}amino)-4,6-dihydrothieno[2,3-c]furan-3-carboxylic acid The title compound was prepared as described in example 43A substituting the product from Example 47 for the product from Example 42B. LC/MS (APCI) m/z 380.2 (M+H)⁺.

Example 48B (1S,4R)—N-{3-[(3,3-difluoroazetidin-1-yl)carbonyl]-4-methyl-4,6-dihydrothieno[2,3-c]furan-2-yl}-4,7,7-trimethyl-3-oxo-2-oxabicyclo[2.2.1]heptane-1-carboxamide The title compound prepared as described in Example 43B substituting the product of Example 48A for the product of Example 43A. ¹H NMR (300 MHz, CDCl₃) δ ppm 0.99 (d, J=7.8 Hz, 3H) 1.12-1.19 (m, 6H) 1.41 (dd, J=6.4, 2.0 Hz, 3H) 1.69-1.82 (m, 1H) 1.91-2.11 (m, 2H) 2.48-2.68 (m, 1H) 4.30 (ddd, J=22.7, 11.5, 6.1 Hz, 2H) 4.55-4.75 (m, 2H) 4.97-5.12 (m, 2H) 5.27-5.39 (m, 1H) 11.50 (d, J=10.2 Hz, 1H). MS (DCI/NH₃) m/z 455.1 (M+H)⁺.

Example 49 ethyl 2-{[5-chloro-2-(trifluoromethyl)benzoyl]amino}-4-methyl-4,6-dihydrothieno[2,3-c]furan-3-carboxylate The title compound was prepared from the product of Example 1A and commercially available 5-chloro-2-(trifluoromethyl)benzoyl chloride using the procedure described for Example 1B. ¹H NMR (DMSO-d₆, 300 MHz) δ 1.29 (t, J=7.1 Hz, 3H), 1.40 (d, J=6.1 Hz, 3H), 4.18-4.36 (m, 2H), 4.87-4.92 (m, 1H), 5.00-5.06 (m, 1H), (dd, J=5.26-5.34 (m, 1H), 7.86-8.01 (m, 3H), 11.32 (br s, 1H). MS (ESI⁺) m/z 434 (M+H)⁺; Anal. calcd. for $C_{18}H_{15}ClF_3NO_4S$: C, 49.83; H, 3.49; N, 3.23. Found: C, 49.88; H, 3.14; N, 3.17.

Example 50

3-chloro-N-{3-[(3,3-difluoroazetidin-1-yl)carbonyl]-4-methyl-4,6-dihydrothieno[2,3-c]furan-2-yl}-2-fluoro-6-(trifluoromethyl)benzamide

Example 50A

2-{[3-chloro-2-fluoro-6-(trifluoromethyl)benzoyl]amino}-4-methyl-4,6-dihydrothieno[2,3-c]furan-3-carboxylic acid The title compound was prepared from the product of Example 6 using the procedure described for Example 2A. LC/MS (ESI$^+$) m/z 424 (M+H)$^+$.

Example 50B 3-chloro-N-{3-[(3,3-difluoroazetidin-1-yl)carbonyl]-4-methyl-4,6-dihydrothieno[2,3-c]furan-2-yl}-2-fluoro-6-(trifluoromethyl)benzamide The title compound was prepared from the product of Example 50A and commercially available 3,3-difluoroazetidine hydrochloride by the procedure described for Example 2B. $^1$H NMR (DMSO-d$_6$, 300 MHz) δ 1.30 (d, J=6.4 Hz, 3H), 4.30-4.51 (m, 4H), 4.89-5.02 (m, 2H), 5.17-5.26 (m, 1H), 7.80 (d, J=8.5 Hz, 1H), 8.03 (dd, J=8.0, 8.0 Hz, 1H), 11.85 (br s, 1H). MS (ESI$^+$) m/z 499 (M+H)$^+$. Anal. calcd. for C$_{19}$H$_{13}$ClF$_6$N$_2$O$_3$S: C, 45.75; H, 2.63; N, 5.62. Found: C, 46.17; H, 2.51; N, 5.33.

Example 51

3-chloro-2-fluoro-N-{3-[(3-methoxyazetidin-1-yl)carbonyl]-4-methyl-4,6-dihydrothieno[2,3-c]furan-2-yl}-6-(trifluoromethyl)benzamide The title compound was prepared from the product of Example 50A and commercially available 3-methoxyazetidine hydrochloride by the procedure described for Example 2B. $^1$H NMR (DMSO-d$_6$, 300 MHz) δ 1.29 (d, J=6.4 Hz, 3H), 3.19 (s, 3H), 3.71-3.77 (m, 1H), 3.80-3.87 (m, 1H), 4.02-4.09 (m, 1H), 4.14-4.22 (m, 2H), 4.88-5.01 (m, 2H). 5.14-5.22 (m, 1H), 7.78 (d, J=9.1 Hz, 1H), 8.02 (dd, J=8.0, 8.0 Hz, 1H), 11.82 (br s, 1H). MS (ESI$^+$) m/z 493 (M+H)$^+$. Anal. calcd. for C$_{20}$H$_{17}$ClF$_4$N$_2$O$_4$S: C, 48.74; H, 3.48; N, 5.68. Found: C, 48.43; H, 3.22; N, 5.43.

Example 52

2-fluoro-N-[4-methyl-3-(tetrahydro-2H-pyran-4-ylcarbonyl)-4,6-dihydrothieno[2,3-c]furan-2-yl]-6-(trifluoromethyl)benzamide

Example 52A (2-amino-4-methyl-4,6-dihydrothieno[2,3-c]furan-3-yl)(tetrahydro-2H-pyran-4-yl)methanone The title compound was prepared from 3-oxo-3-(tetrahydro-2H-pyran-4-yl)propanenitrile and 2-methyltetrahydrofuran-3-one by the procedure described for Example 1A. LC/MS (ESI$^+$) m/z 268 (M+H)$^+$.

Example 52B 2-fluoro-N-[4-methyl-3-(tetrahydro-2H-pyran-4-ylcarbonyl)-4,6-dihydrothieno[2,3-c]furan-2-yl]-6-(trifluoromethyl)benzamide The title compound was prepared from the product of Example 52A and 2-fluoro-6-trifluoromethylbenzoyl chloride by the procedure described for Example 1B. $^1$H NMR (DMSO-d$_6$, 300 MHz) δ 1.33 (d, J=6.1 Hz, 3H), 1.64-1.71 (m, 4H), 3.01-3.10 (m, 2H), 3.34-3.43 (m, 1H), 3.82-3.93 (m, 2H), 4.89-5.04 (m, 2H), 5.36-5.45 (m, 1H), 7.75-7.85 (m, 3H), 12.08 (br s, 1H). MS (ESI$^+$) m/z 493 (M+H)$^+$.

Example 53

5-chloro-N-{3-[(3,3-difluoroazetidin-1-yl)carbonyl]-4-methyl-4,6-dihydrothieno[2,3-c]furan-2-yl}-2-(trifluoromethyl)benzamide

Example 53A

2-{[5-chloro-2-(trifluoromethyl)benzoyl]amino}-4-methyl-4,6-dihydrothieno[2,3-c]furan-3-carboxylic acid The title compound was prepared from the product of Example 49 using the procedure described for Example 2A. LC/MS (ESI$^+$) m/z 406 (M+H)$^+$.

Example 53B 5-chloro-N-{3-[(3,3-difluoroazetidin-1-yl)carbonyl]-4-methyl-4,6-dihydrothieno[2,3-c]furan-2-yl}-2-(trifluoromethyl)benzamide The title compound was prepared from the product of Example 53A and commercially available 3,3-difluoroazetidine hydrochloride by the procedure described for Example 2B. $^1$H NMR (DMSO-d$_6$, 300 MHz) δ 1.30 (d, J=6.4 Hz, 3H), 4.30-4.53 (m, 4H), 4.89-5.01 (m, 2H), 5.18-5.27 (m, 1H), 7.82-7.95 (m, 3H), 11.60 (br s, 1H). MS (ESI$^+$) m/z 481 (M+H)$^+$. Anal. calcd. for C$_{19}$H$_{14}$ClF$_5$N$_2$O$_3$S: C, 47.46; H, 2.93; N, 5.83. Found: C, 47.38; H, 2.52; N, 5.72.

Example 54 ethyl 2-[(2,6-dimethylbenzoyl)amino]-4-methyl-4,6-dihydrothieno[2,3-c]furan-3-carboxylate The title compound was prepared from the product of Example 1A and 2,6-dimethylbenzoyl chloride by the procedure described for Example 1B. $^1$H NMR (DMSO-d$_6$, 300 MHz) δ 1.26 (t, J=7.1 Hz, 3H), 1.40 (d, J=6.1 Hz, 3H), 2.27 (s, 6H), 4.15-4.33 (m, 2H), 4.87-4.91 (m, 1H), 5.00-5.05 (m, 1H), 5.24-5.33 (m, 1H), 7.16 (d, J=8.1 Hz, 2H), 7.31 (dd, J=8.1, 6.7 Hz, 1H), 11.01 (br s, 1H). MS (ESI$^+$) m/z 360 (M+H)$^+$. Anal. calcd. for C$_{19}$H$_{14}$ClF$_5$N$_2$O$_3$S: C, 63.49; H, 5.89; N, 3.90. Found: C, 63.34; H, 5.93; N, 3.84.

Example 55

2-{[2-fluoro-6-(trifluoromethyl)benzoyl]amino}-4,4,6,6-tetramethyl-N-(3,3,3-trifluoropropyl)-4,6-dihydrothieno[2,3-c]furan-3-carboxamide The title compound was prepared from the product of Example 45A and commercially available 3,3,3-trifluoropropylamine hydrochloride by the procedure described for Example 2B. $^1$H NMR (DMSO-$d_6$, 300 MHz), 1.43 (s, 6H), 1.48 (s, 6H), 2.39-3.50 (m, 2H), 3.35-3.42 (m, 2H), 7.68-7.81 (m, 3H), 8.31 (t, J=5.4 Hz, 1H), 11.53 (br s, 1H). MS (ESI$^+$) m/z 527 (M+H)$^+$. Anal. calcd. for $C_{22}H_{21}F_7N_2O_3S$: C, 50.19; H, 4.02; N, 5.32. Found: C, 50.30; H, 4.13; N, 5.00.

Example 56

N-cyclobutyl-2-{[2-fluoro-6-(trifluoromethyl)benzoyl]amino}-4,4,6,6-tetramethyl-4,6-dihydrothieno[2,3-c]furan-3-carboxamide The title compound was prepared from the product of Example 45A and commercially available cyclobutylamine using the procedure described for Example 2B. $^1$H NMR (DMSO-$d_6$, 300 MHz) δ 1.43 (s, 6H), 1.47 (s, 6H), 1.55-1.68 (m, 2H), 1.87-2.01 (m, 2H), 2.10-2.20 (m 2H), 4.21-4.35 (m, 1H), 7.66-7.80 (m, 3H), 8.28 (d, J=7.5 Hz, 1H), 11.55 (br s, 1H). MS (ESI$^+$) m/z 485 (M+H)$^+$. Anal. calcd. for $C_{23}H_{24}F_4N_2O_3S$: C, 57.02; H, 4.99; N, 5.78. Found: C, 57.05; H, 5.02; N, 5.81.

Example 57

N-cyclopentyl-2-{[2-fluoro-6-(trifluoromethyl)benzoyl]amino}-4,4,6,6-tetramethyl-4,6-dihydrothieno[2,3-c]furan-3-carboxamide The title compound was prepared from the product of Example 45A and commercially available cyclopentylamine by the procedure described for Example 2B. $^1$H NMR (DMSO-$d_6$, 300 MHz) δ 1.43 (s, 6H), 1.47 (s, 6H), 1.43-1.50 (m, 4H), 1.55-1.66 (m, 2H), 1.74-1.82 (m, 2H), 4.02-4.14 (m, 1H), 7.67-7.77 (m, 3H), 8.04 (d, J=7.5 Hz, 1H), 11.53 (br s, 1H). MS (ESI$^+$) m/z 499 (M+H)$^+$. Anal. calcd. for $C_{24}H_{26}F_4N_2O_3S$: C, 57.82; H, 5.26; N, 5.62. Found: C, 57.77; H, 5.32; N, 5.53.

Example 58

2-{[2-fluoro-6-(trifluoromethyl)benzoyl]amino}-N-isobutyl-4,4,6,6-tetramethyl-4,6-dihydrothieno[2,3-c]furan-3-carboxamide The title compound was prepared from the product of Example 45A and commercially available isobutylamine using the procedure described for Example 2B. $^1$H NMR (DMSO-$d_6$, 300 MHz) δ 0.85 (d, J=6.8 Hz, 6H), 1.45 (s, 6H), 1.48 (s, 6H), 1.76 (sept, J=6.8 Hz, 1H), 2.99 (t, J=6.4 Hz, 2H), 7.67-7.81 (m, 3H), 8.05 (t, J=5.9 Hz, 1H), 11.49 (br s, 1H). MS (ESI$^+$) m/z 487 (M+H)$^+$. Anal. calcd. for $C_{23}H_{26}F_4N_2O_3S$: C, 56.78; H, 5.39; N, 5.76. Found: C, 57.06; H, 5.57; N, 5.68.

Example 59

2-{[2-fluoro-6-(trifluoromethyl)benzoyl]amino}-4,4,6,6-tetramethyl-N-[(2S)-tetrahydrofuran-2-ylmethyl]-4,6-dihydrothieno[2,3-c]furan-3-carboxamide The title compound was prepared from the product of Example 45A and commercially available (S)-2-aminomethyltetrahydrofuran using the procedure described for Example 2B. $^1$H NMR (DMSO-$d_6$, 300 MHz) δ 1.45 (s, 6H), 1.48 (s, 6H), 1.50-1.58 (m, 2H), 1.66-0.191 (m, 3H), 3.13-3.29 (m, 2H), 3.39-3.46 (m, 1H), 3.60-3.67 (m, 1H), 3.85-3.94 (m, 1H), 7.69-7.82 (m, 3H), 8.03 (t, J=5.8 Hz, 1H), 11.42 (br s, 1H). MS (ESI$^+$) m/z 515 (M+H)$^+$. Anal. calcd. for $C_{24}H_{26}F_4N_2O_4S$: C, 56.02; H, 5.09; N, 5.44. Found: C, 55.98; H, 5.05; N, 5.48.

Example 60

N-(cyclopropylmethyl)-2-{[2-fluoro-6-(trifluoromethyl)benzoyl]amino}-4,4,6,6-tetramethyl-4,6-dihydrothieno[2,3-c]furan-3-carboxamide The title compound was prepared from the product of Example 45A and commercially available aminomethylcyclopropane using the procedure described for Example 2B. $^1$H NMR (DMSO-$d_6$, 300 MHz) δ 0.15-0.20 (m, 2H), 0.35-0.41 (m, 2H), 0.91-1.01 (m, 1H), 1.46 (s, 6H), 1.48 (s, 6H), 3.03 (dd, J=6.1, 6.0 Hz, 2H), 7.67-7.80 (m, 3H), 8.11 (t, J=5.6 Hz, 1H), 11.56 (br s, 1H). MS (ESI$^+$) m/z 485 (M+H)$^+$.

Example 61

2-{[2-fluoro-6-(trifluoromethyl)benzoyl]amino}-4,4,6,6-tetramethyl-N-[(2R)-tetrahydrofuran-2-ylmethyl]-4,6-dihydrothieno[2,3-c]furan-3-carboxamide The title compound was prepared from the product of Example 45A and commercially available (R)-2-aminomethyltetrahydrofuran using the procedure described for Example 2B. $^1$H NMR (DMSO-$d_6$, 300 MHz) δ 1.45 (s, 6H), 1.48 (s, 6H), 1.50-1.58 (m, 2H), 1.66-0.191 (m, 3H), 3.13-3.29 (m, 2H), 3.39-3.46 (m, 1H), 3.60-3.67 (m, 1H), 3.85-3.94 (m, 1H), 7.69-7.82 (m, 3H), 8.03 (t, J=5.8 Hz, 1H), 11.42 (br s, 1H). MS (ESI$^+$) m/z 515 (M+H)$^+$.

Example 62 propyl 4,4,6,6-tetramethyl-2-{[2-(trifluoromethyl)benzoyl]amino}-4,6-dihydrothieno[2,3-c]furan-3-carboxylate

Example 62A propyl 2-amino-4,4,6,6-tetramethyl-4,6-dihydrothieno[2,3-c]furan-3-carboxylate The title compound was prepared from commercially available propyl cyanoacetate and 2,2,5,5-tetramethyldihydro-furan-3-one using the procedure described for Example 1A. LC/MS (ESI$^+$) m/z 300 (M+H)$^+$.

Example 62B propyl 4,4,6,6-tetramethyl-2-{[2-(trifluoromethyl)benzoyl]amino}-4,6-dihydrothieno[2,3-c]furan-3-carboxylate The title compound was prepared from the product of Example 62A and commercially available 2-trifluoromethylbenzoyl chloride using the procedure described for Example 1B. $^1$H NMR (DMSO-$d_6$, 300 MHz) δ 0.90 (t, J=7.5 Hz, 3H), 1.50 (s, 6H), 1.54 (s, 6H), 1.63-1.75 (m, 2H), 4.22 (t, J=6.8 Hz, 2H), 7.79-7.95 (m, 4H), 11.47 (br s, 1H). MS (ESI$^+$) m/z 456 (M+H)$^+$. Anal. calcd. for $C_{22}H_{24}F_3NO_4S$: C, 58.01; H, 5.31; N, 3.08. Found: C, 57.97; H, 5.37; N, 3.04.

Example 63 propyl 2-{[2-fluoro-6-(trifluoromethyl)benzoyl] amino}-4,4,6,6-tetramethyl-4,6-dihydrothieno[2,3-c] furan-3-carboxylate The title compound was prepared from the product of Example 62A and commercially available 2-fluoro-6-(trifluoromethyl)benzoyl chloride using the procedure described for Example 1B. $^1$H NMR (DMSO-$d_6$, 300 MHz) δ 0.90 (t, J=7.5 Hz, 3H), 1.49 (s, 6H), 1.54 (s, 6H), 1.62-1.74 (m, 2H), 4.20 (t, J=6.7 Hz, 2H), 7.74-7.88 (m, 3H), 11.61 (br s, 1H). MS (ESI$^+$) m/z 474 (M+H)$^+$. Anal. calcd. for $C_{22}H_{23}F_4NO_4S$: C, 55.81; H, 4.90; N, 2.96. Found: C, 56.11; H, 5.04; N, 3.01.

Example 64

2-{[2-fluoro-6-(trifluoromethyl)benzoyl]amino}-N-isopropyl-4,4,6,6-tetramethyl-4,6-dihydrothieno[2,3-c]furan-3-carboxamide The title compound was prepared from the product of Example 45A and commercially available isopropylamine by the procedure described for Example 2B. $^1$H NMR (DMSO-$d_6$, 300 MHz) δ 1.08 (d, J=6.4 Hz, 6H), 1.44 (s, 6H), 1.47 (s, 6H), 3.89-4.00 (m, 1H), 7.66-7.80 (m, 3H), 7.91 (d, J=7.8 Hz, 1H), 11.51 (br s, 1H). MS (ESI$^+$) m/z 473 (M+H)$^+$. Anal. calcd. for $C_{22}H_{24}F_4N_2O_3S$: C, 55.92; H, 5.12; N, 5.93. Found: C, 56.03; H, 5.26; N, 5.89.

Example 65

2-{[2-fluoro-6-(trifluoromethyl)benzoyl]amino}-4,4,6,6-tetramethyl-N-prop-2-ynyl-4,6-dihydrothieno[2,3-c]furan-3-carboxamide The title compound was prepared from the product of Example 45A and commercially available propargylamine hydrochloride using the procedure described for Example 2B. $^1$H NMR (DMSO-$d_6$, 300 MHz) δ 1.44 (s. 6H), 1.48 (s, 6H), 3.06-3.08 (m, 1H), 3.90-3.93 (m, 2H), 7.65-7.81 (m, 3H), 8.55 (t, J=5.6 Hz, 1H), 11.58 (br s, 1H). MS (ESI$^+$) m/z 469 (M+H)$^+$. Anal. calcd. for $C_{22}H_{20}F_4N_2O_3S$: C, 56.40; H, 4.30; N, 5.98. Found: C, 56.36; H, 4.27; N, 5.94.

Example 66

2-{[2-fluoro-6-(trifluoromethyl)benzoyl]amino}-N-[(2S)-2-hydroxypropyl]-4,4,6,6-tetramethyl-4,6-dihydrothieno[2,3-c]furan-3-carboxamide The title compound was prepared from the product of Example 45A and commercially available (S)-2-hydroxypropylamine using the procedure described for Example 2B. $^1$H NMR (DMSO-$d_6$, 300 MHz) δ 1.01 (d, J=6.1 Hz, 3H), 1.48 (s, 6H), 1.46 (s, 6H), 3.07-3.20 (m, 2H), 3.65-3.73 (m, 1H), 4.68 (d, J=4.4 Hz, 1H), 7.68-7.81 (m, 4H), 11.60 (br s, 1H). MS (ESI$^+$) m/z 489 (M+H)$^+$. Anal. calcd. for $C_{22}H_{24}F_4N_2O_4S$: C, 54.09; H, 4.95; N, 5.73. Found: C, 53.91; H, 4.89; N, 5.38.

Example 67 ethyl 2-{[4-fluoro-2-(trifluoromethyl)benzoyl] amino}-4,4,6,6-tetramethyl-4,6-dihydrothieno[2,3-c] furan-3-carboxylate The title compound was prepared from the product of Example 18A and commercially available 4-fluoro-2-(trifluoromethyl)benzoyl chloride using the procedure described for Example 1B. $^1$H NMR (DMSO-$d_6$, 300 MHz) δ 1.30 (t, J=7.1 Hz, 3H), 1.49 (s, 6H), 1.54 (s, 6H), 4.30 (q, J=7.1 Hz, 2H), 7.76 (ddd, J=9.1, 8.6, 2.4 Hz, 1H), 7.88 (dd, J=9.3, 2.5 Hz, 1H), 7.96 (dd, J=8.6, 5.3 Hz, 1H), 11.48 (br s, 1H). MS (ESI$^+$) m/z 460 (M+H)$^+$. Anal. calcd. for $C_{21}H_{21}F_4NO_4S$: C, 54.90; H, 4.61; N, 3.05. Found: C, 54.84; H, 4.60; N, 3.02.

Example 68 ethyl 2-{[5-fluoro-2-(trifluoromethyl)benzoyl] amino}-4,4,6,6-tetramethyl-4,6-dihydrothieno[2,3-c] furan-3-carboxylate The title compound was prepared from the product of Example 18A and commercially available 5-fluoro-2-(trifluoromethyl)benzoyl chloride using the procedure described for Example 1B. $^1$H NMR (DMSO-$d_6$, 300 MHz) δ 1.30 (t, J=7.1 Hz, 3H), 1.54 (s, 6H), 1.49 (s, 6H), 4.30 (q, J=7.1 Hz, 2H), 7.63-7.70 (m, 1H), 7.82 (dd, J=8.6, 2.5 Hz, 1H), 8.01 (dd, J=8.8, 5.1 Hz, 1H), 11.48 (br s, 1H). MS (ESI$^+$) m/z 460 (M+H)$^+$. Anal. calcd. for $C_{21}H_{21}F_4NO_4S$: C, 54.90; H, 4.61; N, 3.05. Found: C, 54.72; H, 4.68; N, 2.98.

Example 69

2-{[2-fluoro-6-(trifluoromethyl)benzoyl]amino}-N-(2-hydroxyethyl)-4,4,6,6-tetramethyl-4,6-dihydrothieno[2,3-c]furan-3-carboxamide The title compound was prepared from the product of Example 45A and commercially available 2-hydroxyethylamine using the procedure described for Example 2B. $^1$H NMR (DMSO-$d_6$, 300 MHz) δ 1.45 (s, 6H), 1.48 (s, 6H), 3.24 (q, J=6.2 Hz, 2H), 3.43 (q, J=5.6 Hz, 2H), 4.65 (t, J=5.6 Hz, 1H), 7.68-7.81 (m, 3H), 7.89 (t, J=5.6 Hz, 1H), 11.58 (br s, 1H). MS (ESI$^+$) m/z 475 (M+H)$^+$.

Example 70

2-{[2-fluoro-6-(trifluoromethyl)benzoyl]amino}-N-(3-hydroxypropyl)-4,4,6,6-tetramethyl-4,6-dihydrothieno[2,3-c]furan-3-carboxamide The title compound was prepared from the product of Example 45A and commercially available 3-hydroxypropylamine using the procedure described for Example 2B. $^1$H NMR (DMSO-$d_6$, 300 MHz) δ 1.44 (s, 6H), 1.47 (s, 6H), 1.56-1.65 (m, 2H), 3.18-3.25 (m, 2H), 3.37-3.44 (m, 2H), 4.43 (t, J=4.8 Hz, 1H), 7.67-7.80 (m, 3H), 8.01 (t, J=5.3 Hz, 1H), 11.57 (br s, 1H). MS (ESI$^+$) m/z 489 (M+H)$^+$. Anal. calcd. for $C_{22}H_{24}F_4N_2O_4S$: C, 54.09; H, 4.95; N, 5.73. Found: C, 53.87; H, 4.86; N, 5.64.

Biological Data

In Vitro Methods

The $CB_1$ and $CB_2$ radioligand binding assays described herein are utilized to determine the selectivity of compounds of the present invention for binding to $CB_2$ relative to $CB_1$ receptors.

Human $CB_2$ Radioligand Binding Assays:

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (1 nM to 10 μM) of displacing ligands. The addition of 10 μM unlabeled CP-55,940 (Tocris, Ellisville, Mo.) was used to assess non-specific binding.

Representative compounds of the present invention bound to $CB_2$ receptors with a $K_i$ of less than about 1,000 nM, preferably less than 400 nM, more preferably less than 200 nM and, most preferably lower than 100 nM.

Human $CB_1$ Radioligand Binding Assay:

HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding. Representative compounds of the present invention bound to $CB_1$ receptors with $K_i$ of about 10 folds to about 1000 folds higher than that for $CB_2$ receptors. These results show that the compounds of the present invention preferably bind to $CB_2$ receptors, therefore are selective ligands for the $CB_2$ receptor.

In Vivo Methods:

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incisional Model of Postoperative Pain

A skin incision model of postoperative pain was produced using the procedures described previously described (Brennan et al., 1996, Pain, 64, 493). All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55). Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient Analysis of Experimental Observations, Ann. Rev. Pharmacol. Toxicol., 20, 441).

Representative compounds of the present invention showed a statistically significant change in paw withdrawal latency versus a saline vehicle at less than about 300 micromoles/kg in the incisional model of postoperative pain. In a more preferred embodiment, compounds of the present invention showed efficacy at less than about 50 micromoles/kg in the incisional model of postoperative pain.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) can be used to test the compounds of the present invention The left L5 and L6 spinal nerves of the rat are isolated adjacent to the vertebral column and tightly ligated with a 5-0 silk suture distal to the DRG, and care is taken to avoid injury of the L4 spinal nerve. Sham rats undergo the same procedure, but without nerve ligation. All animals are allowed to recover for at least one week and not more than three weeks prior to assessment of tactile allodynia.

Tactile allodynia is measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55). Rats are placed into inverted individual plastic containers (20×12.5×20 cm) on top of a suspended wire mesh grid, and acclimated to the test chambers for 20 minutes. The von Frey filaments are presented perpendicularly to the plantar surface of the selected hind paw, and then hold in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold is determined using an up-down procedure (Dixon, W. J., 1980, Efficient Analysis of Experimental Observations, Ann. Rev. Pharmacol. Toxicol., 20, 441). Only rats with a baseline threshold score of less that 4.25 g are used in this study, and animals demonstrating motor deficit are excluded. Tactile allodynia thresholds are also assessed in several control groups, including naive, sham-operated, and saline infused animals as well as in the contralateral paws of nerve-injured rats. Representative compounds of the present invention showed a statistically significant change in paw withdrawal latency versus a saline vehicle at less than about 300 micromoles/kg in the spinal nerve ligation model. In a more preferred embodiment, compounds of the present invention showed efficacy of less than about 50 micromoles/kg in the spinal nerve ligation model.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia expresses a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends in Neuroscience, 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets —CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment of pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators have utility for the treatment or prophylaxis of cardiovascular disease and the development of myocardial infarction.

The present invention also provides pharmaceutical compositions that comprise compounds of the present invention. The pharmaceutical compositions comprise compounds of the present invention or pharmaceutically acceptable salt thereof, in combination with one or more pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally" as used herein, refers to modes of administration that include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

When used in the above or other treatments, a therapeutically effective amount of one of the compounds of the present invention can be employed in pure form or, where such forms exist, in pharmaceutically acceptable salt, or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt" as used herein, means salts derived from inorganic or organic acids. The salts can be prepared in situ during the final isolation and purification of compounds of Formula (I) or separately by reacting the free base of a compound of Formula (I) with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, malate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of Formula (I), for example, by hydrolysis in blood.

The present invention contemplates compounds of Formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound according to formula (I),

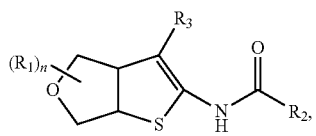

or a pharmaceutically acceptable salt thereof, wherein
n is 0, 1, 2, 3, or 4;
R1, at each occurrence, is independently selected from the group consisting of alkyl, alkoxylalkyl, haloalkyl, hydroxyalkyl, oxo, R4O2C—, RcRdNC(O)—, and RcRdNS(O)2—; two R1 together with the same carbon atom to which they are attached, optionally form a 4-, 5-, or 6-membered monocyclic cycloalkyl;
R2 is selected from the group consisting of aryl, cycloalkyl, heterocycle, and ReRfN—;
R3 is selected from the group consisting of alkyl, alkoxyalkyl, haloalkyl, hydroxyalkyl, R5—C(O)—, R5-C(=N—ORp)—, R6OC(O)—, RgRjNC(O)—, R5-S(O)2—, and RgRjNS(O)2-;
R4 is selected from the group consisting of alkyl, arylalkyl, haloalkyl, and heterocycloalkyl;
R5, at each occurrence, is selected from the group consisting of alkyl, alkoxyalkyl, aryl, cycloalkyl, haloalkyl, heteroaryl, and heterocycle;
R6 is selected from the group consisting of alkyl, arylalkyl, haloalkyl, cycloalkyl, cycloalkylalkyl, heterocycloalkyl, and heteroarylalkyl;
Rc and Rd, at each occurrence, are each independently selected from the group consisting of hydrogen, alkyl, and haloalkyl, or Rc and Rd together with the nitrogen atom to which they are attached form a heterocyclic ring;
Re is selected from the group consisting of hydrogen, alkyl, haloalkyl, cycloalkylalkyl, and alkylcarbonyl;
Rf is selected from the group consisting of hydrogen, alkyl, and haloalkyl;
Rg, at each occurrence, is independently selected from the group consisting of alkyl, alkenyl, alkynyl, cycloalkyl, hydroxyalkyl, alkoxyalkyl, arylalkyl, cycloalkylalkyl, haloalkyl, heteroarylalkyl, and heterocycloalkyl;
Rj, at each occurrence, is independently selected from the group consisting of hydrogen, alkyl, and haloalkyl; and
Rp is selected from the group consisting of hydrogen and alkyl.

2. The compound according to claim 1 or a pharmaceutically acceptable salt thereof, wherein R3 is R5-C(O)—.

3. The compound according to claim 2 or a pharmaceutically acceptable salt thereof, wherein R2 is aryl.

4. The compound according to claim 2 or a pharmaceutically acceptable salt thereof, wherein R2 is cycloalkyl.

5. The compound according to claim 2 or a pharmaceutically acceptable salt thereof, wherein R2 is heterocycle.

6. The compound according to claim 2 or a pharmaceutically acceptable salt thereof, wherein R2 is ReRfN—.

7. The compound according to claim 1 or a pharmaceutically acceptable salt thereof, wherein R3 is R6OC(O)—.

8. The compound according to claim 7 or a pharmaceutically acceptable salt thereof, wherein R2 is aryl.

9. The compound according to claim 7 or a pharmaceutically acceptable salt thereof, wherein R2 is cycloalkyl.

10. The compound according to claim 7 or a pharmaceutically acceptable salt thereof, wherein R2 is heterocycle.

11. The compound according to claim 1 or a pharmaceutically acceptable salt thereof, wherein R3 is RgRjNC(O)—.

12. The compound according to claim 11 or a pharmaceutically acceptable salt thereof, wherein R2 is cycloalkyl.

13. The compound according to claim 11 or a pharmaceutically acceptable salt thereof, wherein R2 is aryl.

14. The compound according to claim 11 or a pharmaceutically acceptable salt thereof, wherein R2 is heterocycle.

15. The compound according to claim 1 or a pharmaceutically acceptable salt thereof, selected from the group consisting of
ethyl 2-{[2-fluoro-6-(trifluoromethyl)benzoyl]amino}-4-methyl-4,6-dihydrothieno[2,3-c]furan-3-carboxylate;
N-{3-[(3,3-difluoroazetidin-1-yl)carbonyl]-4-methyl-4,6-dihydrothieno[2,3-c]furan-2-yl}-2-fluoro-6-(trifluoromethyl)benzamide;
ethyl 4-methyl-2-{[2-(trifluoromethyl)benzoyl]amino}-4,6-dihydrothieno[2,3-c]furan-3-carboxylate;
N-[3-(azetidin-1-ylcarbonyl)-4-methyl-4,6-dihydrothieno[2,3-c]furan-2-yl]-2-fluoro-6-(trifluoromethyl)benzamide;
N-{3-[(3,3-difluoroazetidin-1-yl)carbonyl]-4-methyl-4,6-dihydrothieno[2,3-c]furan-2-yl}-2-(trifluoromethyl)benzamide;
ethyl 2-{[3-chloro-2-fluoro-6-(trifluoromethyl)benzoyl]amino}-4-methyl-4,6-dihydrothieno[2,3-c]furan-3-carboxylate;
2-fluoro-N-{3-[(3-methoxyazetidin-1-yl)carbonyl]-4-methyl-4,6-dihydrothieno[2,3-c]furan-2-yl}-6-(trifluoromethyl)benzamide;
N-(3-benzoyl-4-methyl-4,6-dihydrothieno[2,3-c]furan-2-yl)-2-fluoro-6-(trifluoromethyl)benzamide;
N-[3-(cyclobutylcarbonyl)-4-methyl-4,6-dihydrothieno[2,3-c]furan-2-yl]-2-fluoro-6-(trifluoromethyl)benzamide;
N-[3-(cyclopropylcarbonyl)-4-methyl-4,6-dihydrothieno[2,3-c]furan-2-yl]-2-fluoro-6-(trifluoromethyl)benzamide;
N-[3-(cyclopentylcarbonyl)-4-methyl-4,6-dihydrothieno[2,3-c]furan-2-yl]-2-fluoro-6-(trifluoromethyl)benzamide;
2-chloro-N-[3-(cyclobutylcarbonyl)-4-methyl-4,6-dihydrothieno[2,3-c]furan-2-yl]-6-fluorobenzamide;
N-(3-benzoyl-4-methyl-4,6-dihydrothieno[2,3-c]furan-2-yl)-3-chloro-2-fluoro-6-(trifluoromethyl)benzamide;
N-[3-(cyclobutylcarbonyl)-4-methyl-4,6-dihydrothieno[2,3-c]furan-2-yl]-N'-(1-cyclopropyl-1-methylethyl)urea;
ethyl 2-[(2,6-difluorobenzoyl)amino]-4-methyl-4,6-dihydrothieno[2,3-c]furan-3-carboxylate;
2-fluoro-N-{3-(2-furoyl)-4-methyl-4,6-dihydrothieno[2,3-c]furan-2-yl}-6-(trifluoromethyl)benzamide;

ethyl 2-[(2-chloro-6-fluorobenzoyl)amino]-4-methyl-4,6-dihydrothieno[2,3-c]furan-3-carboxylate;
ethyl 2-{[2-fluoro-6-(trifluoromethyl)benzoyl]amino}-4,4,6,6-tetramethyl-4,6-dihydrothieno[2,3-c]furan-3-carboxylate;
ethyl 2-{[5-chloro-2-(trifluoromethyl)benzoyl]amino}-4,4,6,6-tetramethyl-4,6-dihydrothieno[2,3-c]furan-3-carboxylate;
ethyl 4,4,6,6-tetramethyl-2-{[(2,2,3,3-tetramethylcyclopropyl)carbonyl]amino}-4,6-dihydrothieno[2,3-c]furan-3-carboxylate;
ethyl 2-{[(1-methoxybicyclo[2.2.2]oct-2-yl)carbonyl]amino}-4,4,6,6-tetramethyl-4,6-dihydrothieno[2,3-c]furan-3-carboxylate;
ethyl 4,4,6,6-tetramethyl-2-({[(1S,2R,4R)-2-methylbicyclo[2.2.1]hept-2-yl]carbonyl}amino)-4,6-dihydrothieno[2,3-c]furan-3-carboxylate;
4,4,6,6-tetramethyl-N-propyl-2-{[(2,2,3,3-tetramethylcyclopropyl)carbonyl]amino}-4,6-dihydrothieno[2,3-c]furan-3-carboxamide;
ethyl 4-methyl-2-{[(2,2,3,3-tetramethylcyclopropyl)carbonyl]amino}-4,6-dihydrothieno[2,3-c]furan-3-carboxylate;
ethyl 4-methyl-2-({[(1S,2R,4R)-2-methylbicyclo[2.2.1]hept-2-yl]carbonyl}amino)-4,6-dihydrothieno[2,3-c]furan-3-carboxylate;
N-{3-[(3,3-difluoroazetidin-1-yl)carbonyl]-4-methyl-4,6-dihydrothieno[2,3-c]furan-2-yl}-2,2,3,3-tetramethylcyclopropanecarboxamide;
5-chloro-N-{3-[(3,3-difluoroazetidin-1-yl)carbonyl]-4-methyl-4,6-dihydrothieno[2,3-c]furan-2-yl}-2-methoxybenzamide;
2-fluoro-N-{3-[(3-hydroxyazetidin-1-yl)carbonyl]-4-methyl-4,6-dihydrothieno[2,3-c]furan-2-yl}-6-(trifluoromethyl)benzamide;
N-(3-benzoyl-4-methyl-4,6-dihydrothieno[2,3-c]furan-2-yl)-2,2,3,3-tetramethylcyclopropanecarboxamide;
N-[3-(cyclobutylcarbonyl)-4-methyl-4,6-dihydrothieno[2,3-c]furan-2-yl]-2,2,3,3-tetramethylcyclopropanecarboxamide;
N-[3-(cyclobutylcarbonyl)-4-methyl-4,6-dihydrothieno[2,3-c]furan-2-yl]hexahydro-2,5-methanopentalene-3a(1H)-carboxamide;
N-[3-(cyclopropylcarbonyl)-4-methyl-4,6-dihydrothieno[2,3-c]furan-2-yl]hexahydro-2,5-methanopentalene-3a(1H)-carboxamide;
N-[3-(cyclopentylcarbonyl)-4-methyl-4,6-dihydrothieno[2,3-c]furan-2-yl]hexahydro-2,5-methanopentalene-3a(1H)-carboxamide;
N-[3-(2-furoyl)-4-methyl-4,6-dihydrothieno[2,3-c]furan-2-yl]hexahydro-2,5-methanopentalene-3a(1H)-carboxamide;
N-[3-(cyclobutylcarbonyl)-4-methyl-4,6-dihydrothieno[2,3-c]furan-2-yl]-2,2-dimethyl-4-oxo-3,4-dihydro-2H-pyran-6-carboxamide;
N-[3-(cyclobutylcarbonyl)-4-methyl-4,6-dihydrothieno[2,3-c]furan-2-yl]-2-ethoxybenzamide;
2-chloro-N-[3-(cyclobutylcarbonyl)-4-methyl-4,6-dihydrothieno[2,3-c]furan-2-yl]-5-fluorobenzamide;
N-[3-(cyclobutylcarbonyl)-4-methyl-4,6-dihydrothieno[2,3-c]furan-2-yl]-2-(trifluoromethoxy)benzamide;
ethyl 2-[(2,6-dichlorobenzoyl)amino]-4-methyl-4,6-dihydrothieno[2,3-c]furan-3-carboxylate;
ethyl 4-methyl-2-{[2-oxatricyclo[3.3.1.1~3,7~]dec-1-ylcarbonyl]amino}-4,6-dihydrothieno[2,3-c]furan-3-carboxylate;
N-{3-[(3,3-difluoroazetidin-1-yl)carbonyl]-4-methyl-4,6-dihydrothieno[2,3-c]furan-2-yl}-2-oxatricyclo[3.3.1.1~3,7~]decane-1-carboxamide;
N-{3-[(3,3-difluoroazetidin-1-yl)carbonyl]-4-methyl-4,6-dihydrothieno[2,3-c]furan-2-yl}hexahydro-2,5-methanopentalene-3a(1H)-carboxamide;
2-{[2-fluoro-6-(trifluoromethyl)benzoyl]amino}-4,4,6,6-tetramethyl-N-propyl-4,6-dihydrothieno[2,3-c]furan-3-carboxamide;
2-{[2-fluoro-6-(trifluoromethyl)benzoyl]amino}-N-(2-methoxyethyl)-4,4,6,6-tetramethyl-4,6-dihydrothieno[2,3-c]furan-3-carboxamide;
ethyl 4-methyl-2-({[(1S,4R)-4,7,7-trimethyl-3-oxo-2-oxabicyclo[2.2.1]hept-1-yl]carbonyl}amino)-4,6-dihydrothieno[2,3-c]furan-3-carboxylate;
(1S,4R)-N-{3-[(3,3-difluoroazetidin-1-yl)carbonyl]-4-methyl-4,6-dihydrothieno[2,3-c]furan-2-yl}-4,7,7-trimethyl-3-oxo-2-oxabicyclo[2.2.1]heptane-1-carboxamide;
ethyl 2-{[5-chloro-2-(trifluoromethyl)benzoyl]amino}-4-methyl-4,6-dihydrothieno[2,3-c]furan-3-carboxylate;
3-chloro-N-{3-[(3,3-difluoroazetidin-1-yl)carbonyl]-4-methyl-4,6-dihydrothieno[2,3-c]furan-2-yl}-2-fluoro-6-(trifluoromethyl)benzamide;
3-chloro-2-fluoro-N-{3-[(3-methoxyazetidin-1-yl)carbonyl]-4-methyl-4,6-dihydrothieno[2,3-c]furan-2-yl}-6-(trifluoromethyl)benzamide;
2-fluoro-N-[4-methyl-3-(tetrahydro-2H-pyran-4-ylcarbonyl)-4,6-dihydrothieno[2,3-c]furan-2-yl]-6-(trifluoromethyl)benzamide;
5-chloro-N-{3-[(3,3-difluoroazetidin-1-yl)carbonyl]-4-methyl-4,6-dihydrothieno[2,3-c]furan-2-yl}-2-(trifluoromethyl)benzamide;
ethyl 2-[(2,6-dimethylbenzoyl)amino]-4-methyl-4,6-dihydrothieno[2,3-c]furan-3-carboxylate;
2-{[2-fluoro-6-(trifluoromethyl)benzoyl]amino}-4,4,6,6-tetramethyl-N-(3,3,3-trifluoropropyl)-4,6-dihydrothieno[2,3-c]furan-3-carboxamide;
N-cyclobutyl-2-{[2-fluoro-6-(trifluoromethyl)benzoyl]amino}-4,4,6,6-tetramethyl-4,6-dihydrothieno[2,3-c]furan-3-carboxamide;
N-cyclopentyl-2-{[2-fluoro-6-(trifluoromethyl)benzoyl]amino}-4,4,6,6-tetramethyl-4,6-dihydrothieno[2,3-c]furan-3-carboxamide;
2-{[2-fluoro-6-(trifluoromethyl)benzoyl]amino}-N-isobutyl-4,4,6,6-tetramethyl-4,6-dihydrothieno[2,3-c]furan-3-carboxamide;
2-{[2-fluoro-6-(trifluoromethyl)benzoyl]amino}-4,4,6,6-tetramethyl-N-[(2S)-tetrahydrofuran-2-ylmethyl]-4,6-dihydrothieno[2,3-c]furan-3-carboxamide;
N-(cyclopropylmethyl)-2-{[2-fluoro-6-(trifluoromethyl)benzoyl]amino}-4,4,6,6-tetramethyl-4,6-dihydrothieno[2,3-c]furan-3-carboxamide;
2-{[2-fluoro-6-(trifluoromethyl)benzoyl]amino}-4,4,6,6-tetramethyl-N-[(2R)-tetrahydrofuran-2-ylmethyl]-4,6-dihydrothieno[2,3-c]furan-3-carboxamide;
propyl 4,4,6,6-tetramethyl-2-{[2-(trifluoromethyl)benzoyl]amino}-4,6-dihydrothieno[2,3-c]furan-3-carboxylate;
propyl 2-{[2-fluoro-6-(trifluoromethyl)benzoyl]amino}-4,4,6,6-tetramethyl-4,6-dihydrothieno[2,3-c]furan-3-carboxylate;
2-{[2-fluoro-6-(trifluoromethyl)benzoyl]amino}-N-isopropyl-4,4,6,6-tetramethyl-4,6-dihydrothieno[2,3-c]furan-3-carboxamide;

2-{[2-fluoro-6-(trifluoromethyl)benzoyl]amino}-4,4,6,6-tetramethyl-N-prop-2-ynyl-4,6-dihydrothieno[2,3-c]furan-3-carboxamide;

2-{[2-fluoro-6-(trifluoromethyl)benzoyl]amino}-N-[(2S)-2-hydroxypropyl]-4,4,6,6-tetramethyl-4,6-dihydrothieno[2,3-c]furan-3-carboxamide;

ethyl 2-{[4-fluoro-2-(trifluoromethyl)benzoyl]amino}-4,4,6,6-tetramethyl-4,6-dihydrothieno[2,3-c]furan-3-carboxylate;

ethyl 2-{[5-fluoro-2-(trifluoromethyl)benzoyl]amino}-4,4,6,6-tetramethyl-4,6-dihydrothieno[2,3-c]furan-3-carboxylate;

2-{[2-fluoro-6-(trifluoromethyl)benzoyl]amino}-N-(2-hydroxyethyl)-4,4,6,6-tetramethyl-4,6-dihydrothieno[2,3-c]furan-3-carboxamide; and 2-{[2-fluoro-6-(trifluoromethyl)benzoyl]amino}-N-(3-hydroxypropyl)-4,4,6,6-tetramethyl-4,6-dihydrothieno[2,3-c]furan-3-carboxamide.

16. A pharmaceutical composition comprising a therapeutically effective amount of a compound of formula (I) according to claim 1, or a pharmaceutically acceptable salt thereof, in combination with a pharmaceutically acceptable carrier.

17. A method of treating pain in a mammal in need of such treatment comprising administering to the mammal a therapeutically effective amount of a compound of formula (I) according to claim 1, or a pharmaceutically acceptable salt thereof.

18. A method for treating nociceptive pain in a mammal in need of such treatment comprising administering to the mammal a therapeutically effective amount of a compound of formula (I) according to claim 1, or a pharmaceutically acceptable salt thereof.

19. A method for treating neuropathic pain in a mammal in need of such treatment comprising administering to the mammal a therapeutically effective amount of a compound of formula (I) according to claim 1, or a pharmaceutically acceptable salt thereof.

20. A method for treating a disorder selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of a compound of formula (I) according to claim 1, or a pharmaceutically acceptable salt thereof.

21. A method for providing neuroprotection in a mammal in need of such treatment comprising administering to the mammal a therapeutically effective amount of a compound of formula (I) according to claim 1, or a pharmaceutically acceptable salt thereof.

* * * * *